(12) United States Patent
Brot et al.

(10) Patent No.: US 7,812,050 B2
(45) Date of Patent: Oct. 12, 2010

(54) POLYMORPHIC FORM OF FLUORO-7-(2,2,2-TRIFLUOROETHOXY) PHENOXATHIIN-10,10-DIOXIDE

(75) Inventors: Elisabeth C. A. Brot, Albany, NY (US); Daniel K. Keefe, Jr., Troy, NY (US); Brian P. Haney, Rensselaer, NY (US); Nigel Metcalfe, Rensselaer, NY (US); Grant J. Palmer, Clifton Park, NY (US); Paul K. Isbester, Castleton, NY (US)

(73) Assignee: CeNeRx BioPharma, Inc., Cary, NC (US)

( * ) Notice: Subject to any disclaimer, the term of this patent is extended or adjusted under 35 U.S.C. 154(b) by 566 days.

(21) Appl. No.: 11/773,892

(22) Filed: Jul. 5, 2007

(65) Prior Publication Data

US 2008/0009542 A1    Jan. 10, 2008

Related U.S. Application Data

(60) Provisional application No. 60/819,078, filed on Jul. 7, 2006.

(51) Int. Cl.
*A61K 31/39*    (2006.01)
*C07D 327/08*    (2006.01)
(52) U.S. Cl. .......................... 514/434; 549/16
(58) Field of Classification Search .................. 549/16; 514/434
See application file for complete search history.

(56) References Cited

U.S. PATENT DOCUMENTS 6,110,961 A    8/2000    White et al.

FOREIGN PATENT DOCUMENTS

WO    WO 98/12190 A    3/1998

OTHER PUBLICATIONS

International Search Report issued on the corresponding PCT Application No. PCT/US2007/015533, dated Dec. 4, 2007.

*Primary Examiner*—Bernard Dentz
(74) *Attorney, Agent, or Firm*—Amy H. Fix; Womble Carlyle Sandridge & Rice, PLLC

(57) ABSTRACT

Provided herein is a new form of 3-fluoro-7-(2,2,2-trifluoroethoxy)phenoxathin 10,10-dioxide, which demonstrates higher stability relative to other forms of 3-fluoro-7-(2,2,2-trifluoroethoxy)phenoxathiin-10,10-dioxide. In particular, this new form affords less dosage critical administration of 3-fluoro-7-(2,2,2-trifluoroethoxy)phenoxathin 10,10-dioxide relative to other forms. The new solid form of 3-fluoro-7-(2,2,2-trifluoroethoxy)phenoxathiin-10,10-dioxide has been determined and is provided herein. This new solid form of 3-fluoro-7-(2,2,2-trifluoroethoxy)phenoxathiin-10,10-dioxide can be characterized by any of a number of its properties, including, but not limited to, melting point, differential scanning calorimetry, infrared spectroscopic spectrum or portions thereof, solubility, methods and conditions under which this form is prepared, and/or precipitated from solution, and, when in crystalline form, the crystalline form can be characterized according to the diffraction pattern or portions thereof.

17 Claims, 9 Drawing Sheets

POLYMORPHIC FORM OF FLUORO-7-(2,2,2-TRIFLUOROETHOXY) PHENOXATHIIN-10,10-DIOXIDE

PRIORITY APPLICATIONS

This application claims priority to U.S. Provisional Application Ser. No. 60/819,078, filed Jul. 7, 2006, the entirety of which is hereby incorporated by reference.

BACKGROUND

1. Field of the Invention

The present invention generally relates to a new form of 3-fluoro-7-(2,2,2-trifluoroethoxy)phenoxathiin-10,10-dioxide.

2. Background

Various compounds have been used therapeutically in the treatment of a psychiatric and neurological conditions, especially depression, particularly when characterized by anxiety, obsessional neuroses, or appetite disorders. However, a number of such compounds, for example isocarboxazid, phenelzine and tranylcypromine, are characterized by an undesirable side effect associated with ingestion of food or drink containing a high level of tyramine, for example, certain cheeses. When a patient receiving such a drug ingests such a product, then the patient's blood pressure may be raised, sometimes to a dangerous level. Such patients are therefore instructed to avoid foods and beverages of this nature.

SUMMARY

Provided herein is a new polymorphic form of 3-fluoro-7-(2,2,2-trifluoroethoxy)phenoxathin 10,10-dioxide, which demonstrates improved stability relative to other forms of 3-fluoro-7-(2,2,2-trifluoroethoxy)phenoxathiin-10,10-dioxide. Furthermore, this novel form offers stability and manufacturing advantages as well.

In one embodiment, provided is a polymorphic form of 3-fluoro-7-(2,2,2-trifluoroethoxy)phenoxathiin-10,10-dioxide, characterized as having a melting point at about 169-175° C. In another embodiment, provided is a polymorphic form of 3-fluoro-7-(2,2,2-trifluoroethoxy)phenoxathiin-10,10-dioxide, characterized as being in crystalline form and having an x-ray powder diffraction peak at 2θ=11.0°, using CuKα radiation. Some such embodiments are further characterized as having x-ray powder diffraction peaks at 2θ=20.1° and/or 22.2°, using CuKα radiation. Some such embodiments are further characterized as having an x-ray powder diffraction pattern substantially identical to FIG. 1(a). In another embodiment, provided is a polymorphic form of 3-fluoro-7-(2,2,2-trifluoroethoxy)phenoxathiin-10,10-dioxide, characterized as having an attenuated total reflectance Fourier transform infrared spectrum at 1480-1440 cm-1 substantially identical to FIG. 2(a). In another embodiment, provided is a polymorphic form of 3-fluoro-7-(2,2,2-trifluoroethoxy)phenoxathiin-10,10-dioxide, characterized as having an attenuated total reflectance Fourier transform infrared spectrum at 970-800 cm-1 substantially identical to FIG. 2(a). In another embodiment, provided is a polymorphic form of 3-fluoro-7-(2,2,2-trifluoroethoxy)phenoxathiin-10,10-dioxide, characterized as dissolving at about 75-85° C. in a solution of 10% (v/v) water in acetic acid.

Also provided herein is a composition, wherein at least about 0.1% of the total 3-fluoro-7-(2,2,2-trifluoroethoxy) phenoxathiin-10,10-dioxide is in Form A. Also provided herein is a composition, wherein at least about 0.5% of the total 3-fluoro-7-(2,2,2-trifluoroethoxy)phenoxathiin-10,10-dioxide is in Form A. Also provided herein is a composition, wherein at least about 1% of the total 3-fluoro-7-(2,2,2-trifluoroethoxy)phenoxathiin-10,10-dioxide is in Form A. Also provided herein is a composition, wherein at least about 2% of the total 3-fluoro-7-(2,2,2-trifluoroethoxy)phenoxathiin-10,10-dioxide is in Form A. Also provided herein is a composition, wherein at least about 3% of the total 3-fluoro-7-(2,2,2-trifluoroethoxy)phenoxathiin-10,10-dioxide is in Form A. Also provided herein is a composition, wherein at least about 4% of the total 3-fluoro-7-(2,2,2-trifluoroethoxy)phenoxathiin-10,10-dioxide is in Form A. Also provided herein is a composition, wherein at least about 5% of the total 3-fluoro-7-(2,2,2-trifluoroethoxy)phenoxathiin-10,10-dioxide is in Form A. Also provided herein is a composition, wherein at least about 7% of the total 3-fluoro-7-(2,2,2-trifluoroethoxy) phenoxathiin-10,10-dioxide is in Form A. Also provided herein is a composition, wherein at least about 10% of the total 3-fluoro-7-(2,2,2-trifluoroethoxy)phenoxathiin-10,10-dioxide is in Form A. Also provided herein is a composition, wherein at least about 15% of the total 3-fluoro-7-(2,2,2-trifluoroethoxy)phenoxathiin-10,10-dioxide is in Form A. Also provided herein is a composition, wherein at least about 20% of the total 3-fluoro-7-(2,2,2-trifluoroethoxy)phenoxathiin-10,10-dioxide is in Form A. Also provided herein is a composition, wherein at least about 30% of the total 3-fluoro-7-(2,2,2-trifluoroethoxy)phenoxathiin-10,10-dioxide is in Form A. Also provided herein is a composition, wherein at least about 50% of the total 3-fluoro-7-(2,2,2-trifluoroethoxy)phenoxathiin-10,10-dioxide is in Form A. Also provided herein is a composition, wherein at least about 70% of the total 3-fluoro-7-(2,2,2-trifluoroethoxy)phenoxathiin-10,10-dioxide is in Form A. Also provided herein is a composition, wherein at least about 90% of the total 3-fluoro-7-(2,2,2-trifluoroethoxy)phenoxathiin-10,10-dioxide is in Form A. Also provided herein is a composition, wherein at least about 95% of the total 3-fluoro-7-(2,2,2-trifluoroethoxy)phenoxathiin-10,10-dioxide is in Form A. Also provided herein is a composition, wherein at least about 99% of the total 3-fluoro-7-(2,2,2-trifluoroethoxy)phenoxathiin-10,10-dioxide is in Form A.

Also provided herein is a method of forming Form A of 3-fluoro-7-(2,2,2-trifluoroethoxy)phenoxathiin-10,10-dioxide by (a) dissolving 3-fluoro-7-(2,2,2-trifluoroethoxy)phenoxathiin-10,10-dioxide in a solvent to form a 3-fluoro-7-(2,2,2-trifluoroethoxy)phenoxathiin-10,10-dioxide solution; and (b) adjusting conditions of the 3-fluoro-7-(2,2,2-trifluoroethoxy)phenoxathiin-10,10-dioxide solution to decrease the solubility of 3-fluoro-7-(2,2,2-trifluoroethoxy)phenoxathiin-10,10-dioxide in the solvent. Some such methods further include seeding the 3-fluoro-7-(2,2,2-trifluoroethoxy) phenoxathiin-10,10-dioxide solution with the polymorphic form of any of Claims 1-7. Also provided herein is a method of forming Form A of 3-fluoro-7-(2,2,2-trifluoroethoxy)phenoxathiin-10,10-dioxide by (a) synthesizing 3-fluoro-7-(2,2,2-trifluoroethoxy)phenoxathiin-10,10-dioxide in sufficiently pure form; and (b) precipitating 3-fluoro-7-(2,2,2-trifluoroethoxy)phenoxathiin-10,10-dioxide from solution, whereby said Form A of 3-fluoro-7-(2,2,2-trifluoroethoxy)phenoxathiin-10,10-dioxide is formed. In some such methods, precipitating step is performed under conditions that are preferential for formation of a thermodynamically favored polymorph of 3-fluoro-7-(2,2,2-trifluoroethoxy)phenoxathiin-10,10-dioxide over a kinetically favored polymorph of 3-fluoro-7-(2,2,2-trifluoroethoxy)phenoxathiin-10,10-dioxide.

Also provided are formulations comprising Form A of 3-fluoro-7-(2,2,2-trifluoroethoxy)phenoxathiin-10,10-dioxide or a composition thereof, and a pharmaceutically acceptable carrier. Some such formulations are formulated for oral administration. Some such formulations are in solid form. Some such formulations are a tablet or a capsule.

Also provided are methods of preparing a formulation by providing Form A of 3-fluoro-7-(2,2,2-trifluoroethoxy)phenoxathiin-10,10-dioxide or a composition thereof; and combining said composition with a pharmaceutically acceptable carrier.

Also provided are methods for treating a mammal having a medical, psychiatric and/or neurological condition or disorder comprising: (a) identifying a subject in need of treatment for a mammal having a medical, psychiatric and/or neurological condition; and (b) administering to the subject a pharmaceutically effective amount of Form A of 3-fluoro-7-(2,2, 2-trifluoroethoxy)phenoxathiin-10,10-dioxide or a composition or formulation thereof.

Also provided are methods of forming 3-fluoro-7-(2,2,2-trifluoroethoxy)phenoxathiin-10,10-dioxide, by (a) synthesizing 3-fluoro-7-(2,2,2-trifluoroethoxy)phenoxathiin; and (b) oxidizing 3-fluoro-7-(2,2,2-trifluoroethoxy)phenoxathiin to form 3-fluoro-7-(2,2,2-trifluoroethoxy)phenoxathiin-10, 10-dioxide.

Also provided are methods of forming 3-fluoro-7-(2,2,2-trifluoroethoxy)phenoxathiin-10,10-dioxide by (a) providing 3-fluoro-7-(2,2,2-trifluoroethoxy)phenoxathiin; (b) providing an oxidizing compound; (c) contacting 3-fluoro-7-(2,2,2-trifluoroethoxy)phenoxathiin with the oxidizing compound to form 3-fluoro-7-(2,2,2-trifluoroethoxy)phenoxathiin-10, 10-dioxide.

Also provided is a compound comprising 3-fluoro-7-(2,2, 2-trifluoroethoxy)phenoxathiin or a solvate or a hydrate thereof. Some such compounds are in substantially pure form.

Also provided are methods of forming 3-fluoro-7-(2,2,2-trifluoroethoxy)phenoxathiin, by reacting 5-(2,2,2-trifluoroethoxy)-2-mercaptophenol with 1,4-difluoro-2-nitrobenzene to form 3-fluoro-7-(2,2,2-trifluoroethoxy)phenoxathiin. In some such methods, the 3-fluoro-7-(2,2,2-trifluoroethoxy) phenoxathiin is formed in the presence of base. In some such methods, 5-(2,2,2-trifluoroethoxy)-2-mercaptophenol is formed by hydrolysis of 6-(2,2,2-trifluoroethoxy)benzo[d] [1,3]oxathiol-2-one. In some such methods, the 5-(2,2,2-trifluoroethoxy)-2-mercaptophenol is formed in an aqueous/organic solvent system. In some such methods, the 5-(2,2,2-trifluoroethoxy)-2-mercaptophenol is used in the reacting step while the organic reaction solvent of the aqueous/organic solvent system is still present. In some such methods, 5-(2,2, 2-trifluoroethoxy)-2-mercaptophenol is in an organic solvent mixture comprising the organic reaction solvent and an organic partition solvent.

DETAILED DESCRIPTION

Provided herein is a new polymorphic form of 3-fluoro-7-(2,2,2-trifluoroethoxy)phenoxathin 10,10-dioxide, which demonstrates improved stability relative to other forms of 3-fluoro-7-(2,2,2-trifluoroethoxy)phenoxathiin-10,10-dioxide as well as manufacturing stability.

Compounds and Compositions

A new polymorphic solid form of 3-fluoro-7-(2,2,2-trifluoroethoxy)phenoxathiin-10,10-dioxide has been determined and is provided herein. This new solid form of 3-fluoro-7-(2,2,2-trifluoroethoxy)phenoxathiin-10,10-dioxide, referred to herein as "Form A," can be characterized by any of a number of its properties, including, but not limited to, melting point, infrared spectroscopic spectrum or portions thereof, solubility, differential scanning calorimetry (DSC) and methods and conditions under which this form is prepared and/or precipitated from solution. Form A also can be in crystalline form, and the crystalline form can further be characterized according to the d spacing and diffraction pattern or portions thereof.

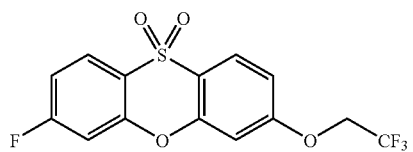

3-fluoro-7-(2,2,2-trifluoroethoxy) phenoxathiin-10,10-dioxide

In particular embodiments, Form A can be characterized as having a melting point at about 169-176° C.; about 170-174° C., about 171-173° C., about 171-172° C., or about 171° C. Form A is distinguishable from at least one other form of 3-fluoro-7-(2,2,2-trifluoroethoxy)phenoxathiin-10,10-dioxide provided herein, referred to herein as Form B, which melts at about 158-163° C., typically about 160-162° C. Form A also can be characterized as containing less than about 1% $H_2O$, about 1%-0.001% $H_2O$, about 0.5%-0.01% $H_2O$, about 0.05%-0.01% $H_2O$, or about 0.02% $H_2O$, as determined by the Karl Fischer method. In addition, Form A can be characterized as having an attenuated total reflectance Fourier transform infrared spectrum at 1480-1440 cm$^{-1}$ substantially identical to FIG. 2(a), having an attenuated total reflectance Fourier transform infrared spectrum at 970-800 cm$^{-1}$ substantially identical to FIG. 2(a), or having an attenuated total reflectance Fourier transform infrared spectrum substantially identical to FIG. 2(a). The attenuated total reflectance Fourier transform infrared spectrum of Form A is distinguishable from the attenuated total reflectance Fourier transform infrared spectrum at 970-800 cm$^{-1}$ and 1480-1440 cm$^{-1}$ of Form B as provided herein, which is substantially identical to FIG. 2(b). Form A can further be characterized as dissolving at about 75-85° C., about 75-80° C., about 75-78° C., or about 75-77° C. in a solvent that is 10% (v/v) water in acetic acid when the ratio (w/v) of compound to solvent is about 1.6 g: 10 mL.

Figure 1A:
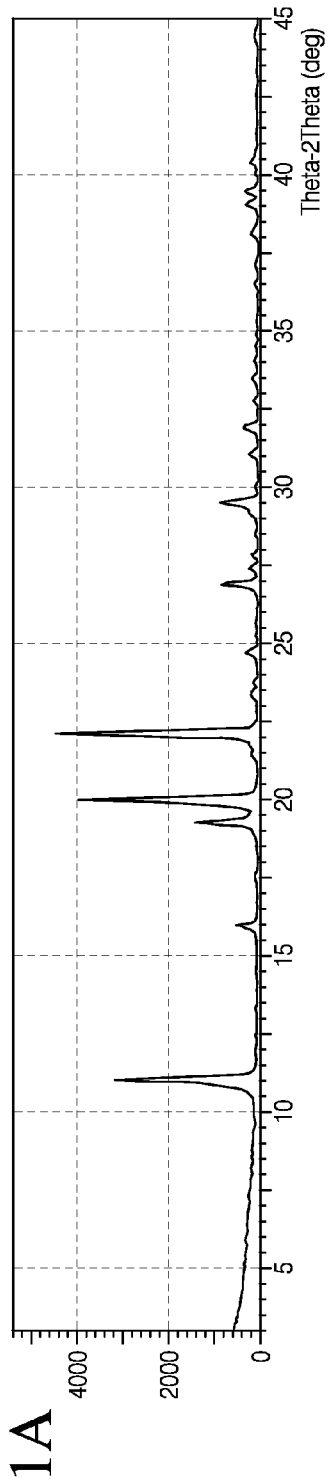
FIG. 1 depicts powder x-ray diffraction patterns of the Form A (FIG. 1(a)) and Form B (FIG. 1(b)) of 3-fluoro-7-(2, 2,2-trifluoroethoxy)phenoxathin 10,10-dioxide, and the product of 3-fluoro-7-(2,2,2-trifluoroethoxy)phenoxathin 10,10-dioxide synthesis as provided in Example 1 (FIG. 1(c)).

In some embodiments, Form A can be in crystalline form. Crystalline Form A can be characterized as having a major x-ray powder diffraction peak at about d spacings 4.0, 4.4 and/or 8.0. Crystalline Form A can be characterized as substantially lacking an x-ray powder diffraction peak at about d spacings 10.3, 7.3, and/or 3.65. Crystalline Form A can be characterized as having a major x-ray powder diffraction peak at about 2θ=11.0°, 20.1°, and/or 22.2°, using CuK$_\alpha$ radiation. Form A also can be characterized as substantially lacking an x-ray powder diffraction peak at 2θ=8.5°, 12.0°, and/or 24.6°, using CuK$_\alpha$ radiation. Form A also can be characterized as having an x-ray powder diffraction pattern substantially identical to FIG. 1(a). The x-ray powder diffraction pattern of Form A is distinguishable from the x-ray powder diffraction properties of Form B as provided herein, which has major peaks at about d spacings 10.3, 7.3, and/or 3.65, and about 2θ=11.0°, 20.1°, and/or 22.2°, using CuK$_\alpha$ radiation, and has an x-ray powder diffraction pattern substantially identical to FIG. 1(b).

Figure 8:
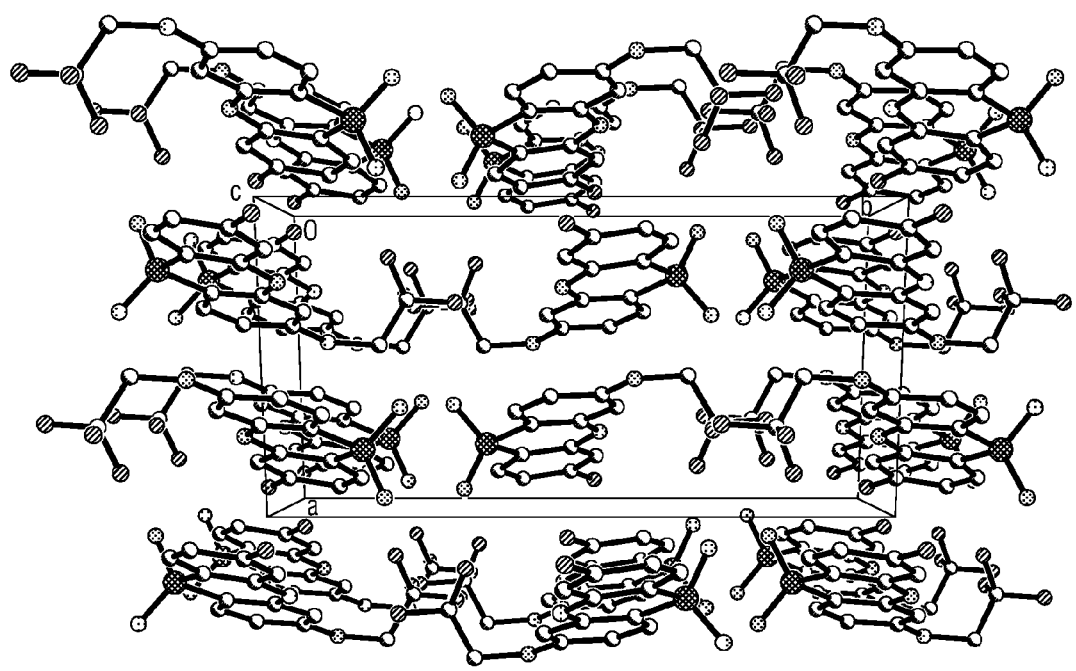
FIG. 8 depicts that crystal packing along the c-axis of crystalline Form A of 3-fluoro-7-(2,2,2-trifluoroethoxy)phenoxathin 10,10-dioxide (i.e., a- and b-axes are in the plane of FIG. 8).
Figure 9:
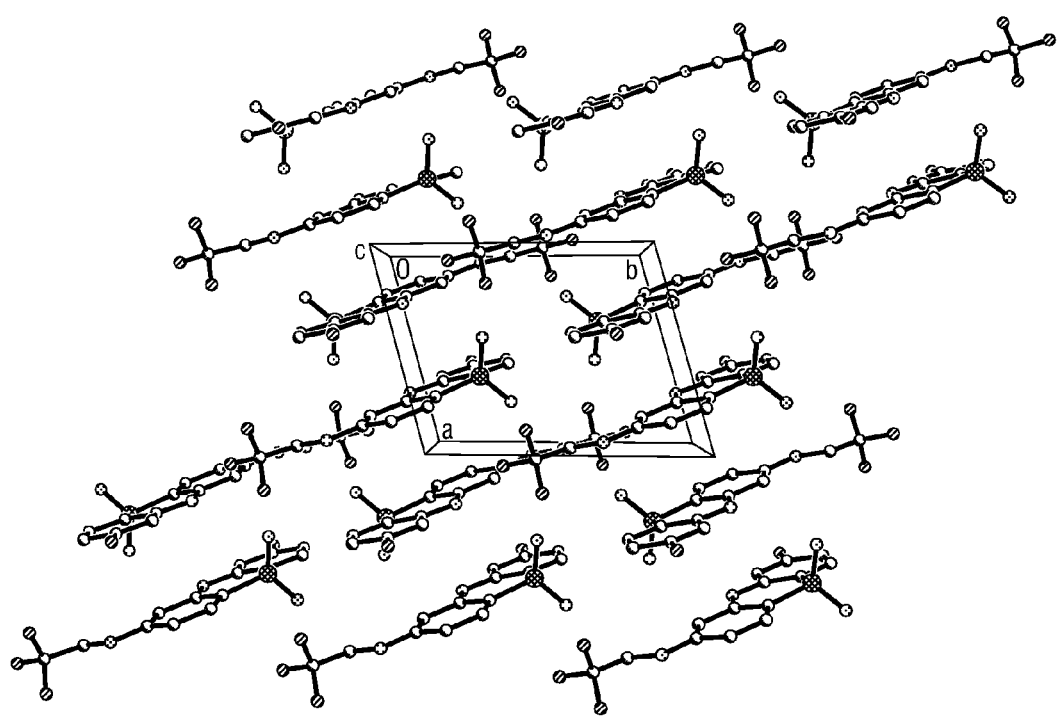
FIG. 9 depicts that crystal packing along the c-axis of crystalline Form B of 3-fluoro-7-(2,2,2-trifluoroethoxy)phenoxathin 10,10-dioxide (i.e., a- and b-axes are in the plane of FIG. 9).

In some embodiments, crystalline Form A can be characterized as a monoclinic crystal, typically having the space group P2$_1$/c. In some such embodiments, crystalline Form A can further be characterized as having unit cell dimensions of about a=8.72 Å, b=16.3 Å, c=9.77 Å, and β=110.4°. In some embodiments, crystalline Form A can be characterized as a crystalline form of 3-fluoro-7-(2,2,2-trifluoroethoxy)phenoxathiin-10,10-dioxide that is not a triclinic crystal. In some embodiments, crystalline Form A can be characterized as a crystalline form of 3-fluoro-7-(2,2,2-trifluoroethoxy)phenoxathiin-10,10-dioxide that does not have unit cell dimensions of about a=7.22 Å, b=9.43 Å, c=10.4 Å, α=80.4°, β=82.6°, and γ=73.8°. In some embodiments, crystalline Form A can be characterized as having the crystal packing as depicted in FIG. 8. In some embodiments, crystalline Form A can be characterized as not having the crystal packing as depicted in FIG. 9.

Form A can be present as the sole form of 3-fluoro-7-(2,2,2-trifluoroethoxy)phenoxathiin-10,10-dioxide or can be present in a mixture of one or more additional forms of 3-fluoro-7-(2,2,2-trifluoroethoxy)phenoxathiin-10,10-dioxide. In embodiments in which Form A is present in a mixture of forms of 3-fluoro-7-(2,2,2-trifluoroethoxy)phenoxathiin-10,10-dioxide, at least about 5-99%, for example, at least about 0.1%, 0.2%, 0.3%, 0.4%, 0.5%, 0.6%, 0.7%, 0.8%, 0.9%, 1%, 1.5%, 2%, 3%, 4%, 5%, 7%, 10%, 20%, 30%, 40%, 50%, 70%, 90%, 93%, 95%, 96%, 97%, 98%, or 99% of the total 3-fluoro-7-(2,2,2-trifluoroethoxy)phenoxathiin-10,10-dioxide in the mixture of forms is Form A. In one exemplary mixture of forms, at least 5% of the mixture is Form A. In another exemplary mixture of forms, at least about 50% of the mixture is Form A. Quantitation of the amounts of each of a variety of forms present in a mixture of forms can be performed by any of a variety of methods known in the art, including, but not limited to, attenuated total reflection Fourier transform infrared (ATR-FTIR) spectroscopy using a partial least square (PLS) algorithm. For example, the region of the ATR-FTIR spectrum between about 950 and 650 cm$^{-1}$ can be used in the PLS calculation, and quantitation of each form can be based on the ATR-FTIR spectrum between about 950 and 650 cm$^{-1}$ for each form in the pure state.

Methods for determining the percent of Form A in a mixture of forms of 3-fluoro-7-(2,2,2-trifluoroethoxy)phenoxathiin-10,10-dioxide are provided herein, and other similar methods will be readily apparent to those skilled in the art. For example, ATR-FTIR spectra were obtained for standard mixtures of Forms A and B of 3-fluoro-7-(2,2,2-trifluoroethoxy)phenoxathiin-10,10-dioxide, and the unique absorbance peaks between 950 and 650 cm$^{-1}$ were analyzed using a Partial Least Squares (PLS) method to generate a linear calibration curve which permitted accurate calculation of weight percentages of Form A and Form B.

Methods of Making

Form A of 3-fluoro-7-(2,2,2-trifluoroethoxy)phenoxathiin-10,10-dioxide can be prepared by any of a variety of methods provided herein. For example, Form A can be prepared synthetically, by slurry-ripening of a non-Form A form of 3-fluoro-7-(2,2,2-trifluoroethoxy)phenoxathiin-10,10-dioxide, or by crystallization. In some embodiments, Form A can be prepared by methods that include adding Form A to a solution or slurry containing 3-fluoro-7-(2,2,2-trifluoroethoxy)phenoxathiin-10,10-dioxide, where the added Form A facilitates formation of additional Form A in the solution or slurry containing 3-fluoro-7-(2,2,2-trifluoroethoxy)phenoxathiin-10,10-dioxide.

Generally, Form A can be prepared under conditions amenable to precipitation of the thermodynamically favored Form A relative to the kinetically favored Form B. In some instances, conditions that result in formation of the kinetically favored Form B are conditions that cause 3-fluoro-7-(2,2,2-trifluoroethoxy)phenoxathiin-10,10-dioxide to rapidly precipitate out of solution. For example, when a solution of 3-fluoro-7-(2,2,2-trifluoroethoxy)phenoxathiin-10,10-dioxide is cooled quickly or has added thereto a liquid in which 3-fluoro-7-(2,2,2-trifluoroethoxy)phenoxathiin-10,10-dioxide has low solubility, typically the kinetically favored Form B will be the predominating solid that precipitates out of solution relative to Form A. In one example, when a solution of 3-fluoro-7-(2,2,2-trifluoroethoxy)phenoxathiin-10,10-dioxide contains impurities that can interfere with precipitation of 3-fluoro-7-(2,2,2-trifluoroethoxy)phenoxathiin-10,10-dioxide, more extreme precipitation conditions (e.g. high cooling rate or addition of liquid in which 3-fluoro-7-(2,2,2-trifluoroethoxy)phenoxathiin-10,10-dioxide has low solubility) can be required that will cause the kinetically favored Form B to be the predominating solid that precipitates out of solution. In some instances, conditions that result in formation of the thermodynamically favored Form A are conditions that cause 3-fluoro-7-(2,2,2-trifluoroethoxy)phenoxathiin-10,10-dioxide to slowly precipitate out of solution or conditions that increase the kinetic favorability of Form A. For example, when a solution of 3-fluoro-7-(2,2,2-trifluoroethoxy)phenoxathiin-10,10-dioxide is cooled slowly or has added thereto an amount of Form A sufficient to "seed" the precipitation, typically the thermodynamically favored Form A will be the predominating solid that precipitates out of solution relative to Form B.

In some embodiments, Form A of 3-fluoro-7-(2,2,2-trifluoroethoxy)phenoxathiin-10,10-dioxide is prepared synthetically. An exemplary method for the preparation of 3-fluoro-7-(2,2,2-trifluoroethoxy)phenoxathiin-10,10-dioxide containing Form A as the major component of the product is provided in Example 1. Briefly, such a method of preparing of 3-fluoro-7-(2,2,2-trifluoroethoxy)phenoxathiin-10,10-dioxide containing Form A as the major component of the product results when sufficient purity of 3-fluoro-7-(2,2,2-trifluoroethoxy)phenoxathiin-10,10-dioxide is attained in the synthesis. In Example 1, the preparation of the precursor to 3-fluoro-7-(2,2,2-trifluoroethoxy)phenoxathiin-10,10-dioxide (Formula IV in Examples 1 and 2) is performed in N,N-dimethylformamide, in contrast to Example 2, where this step is performed in 1-methyl-2-pyrrolidinone. These two different reaction conditions influenced the purity of the intermediate compound of Formula IV, and, as a result, influenced the final purity and form of 3-fluoro-7-(2,2,2-trifluoroethoxy)phenoxathiin-10,10-dioxide. The purity of Formula IV from Example 1 was 97.3%, and the purity of Formula IV from Example 2 was 93.5%. This ultimately led to the final product of Example 1 being primarily Form A of 3-fluoro-7-(2,2,2-trifluoroethoxy)phenoxathiin-10,10-dioxide, and the final product of Example 2 being Form B of 3-fluoro-7-(2,2,2-trifluoroethoxy)phenoxathiin-10,10-dioxide. While the above example identifies dimethylformamide as a desirable solvent in the preparation of the compound of Formula IV, alternative solvents can be used; such solvents typically will have a high boiling point and high polarity, such as, for example, dimethylacetamide, toluene, dioxane and xylenes. Upon formation of the compound of Formula IV, 3-fluoro-7-(2,2,2-trifluoroethoxy)phenoxathiin-10,10-dioxide can be prepared by an oxidation method in which the sulfur atom of the phenoxathiin ring is oxidized. Any of a variety of suitable oxidation methods known in the art can be used, for example, oxidation of the compound of Formula IV with peracetic acid in acetic acid solution.

In some embodiments, 3-fluoro-7-(2,2,2-trifluoroethoxy)phenoxathiin-10,10-dioxide, whether in a single non-Form A form or two or more forms, can be treated such that the amount Form A is increased, or such that the sole form of the 3-fluoro-7-(2,2,2-trifluoroethoxy)phenoxathiin-10,10-dioxide is Form A. Such treatment methods include treatment of 3-fluoro-7-(2,2,2-trifluoroethoxy)phenoxathiin-10,10-dioxide in solid form or treatment of 3-fluoro-7-(2,2,2-trifluoroethoxy)phenoxathiin-10,10-dioxide in solute form. In some such treatment methods, some amount of Form A is added to the solid or to the solution in order to facilitate formation of Form A from the 3-fluoro-7-(2,2,2-trifluoroethoxy)phenoxathiin-10,10-dioxide solute or from the non-Form A 3-fluoro-7-(2,2,2-trifluoroethoxy)phenoxathiin-10,10-dioxide solid.

In some embodiments, solid 3-fluoro-7-(2,2,2-trifluoroethoxy)phenoxathiin-10,10-dioxide can be taken up in liquid as a slurry. The liquid and conditions under which such a slurry will be formed are a liquid and conditions in which not all of the 3-fluoro-7-(2,2,2-trifluoroethoxy)phenoxathiin-10,10-dioxide is dissolved. Any of a variety of liquids, temperatures and other parameters can be used in preparing Form A from a slurry, as will be apparent to one skilled in the art, based on the teachings provided herein. Generally, the slurry conditions will be selected such that 3-fluoro-7-(2,2,2-trifluoroethoxy)phenoxathiin-10,10-dioxide is at least slightly soluble in the solvent (e.g. $H_2O$, acetic acid, or $H_2O$/acetic acid, such as 30% $H_2O$/70% acetic acid, at 20° C.), but is not so soluble that all 3-fluoro-7-(2,2,2-trifluoroethoxy)phenoxathiin-10,10-dioxide dissolves in the solvent. In addition, conditions such as temperature are selected such that 3-fluoro-7-(2,2,2-trifluoroethoxy)phenoxathiin-10,10-dioxide does not degrade during the slurry process. Exemplary liquids in which such a slurry can be formed include, but are not limited to $H_2O$, isopropyl acetate, acetic acid, acetic acid/water (50-95% acetic acid), methyl ethyl ketone, acetone, cumene, and methyl t-butyl ether. Exemplary conditions for forming a slurry of 3-fluoro-7-(2,2,2-trifluoroethoxy)phenoxathiin-10,10-dioxide in $H_2O$, acetic acid or 30% $H_2O$/70% acetic acid include about 0 to 100° C., about 10 to 90° C., about 20 to 75° C., about 20 to 70° C., about 20 to 65° C., about 20 to 60° C., about 20 to 55° C., about 20 to 50° C., about 20 to 45° C., about 20 to 40° C., about 20 to 35° C., or about 20 to 30° C., such as ambient temperature (e.g. about 20 to 25° C.). The amount of time for maintaining such a slurry can be a factor of the solvent, the concentration of 3-fluoro-7-(2,2,2-trifluoroethoxy)phenoxathiin-10,10-dioxide in the slurry, and the amount of 3-fluoro-7-(2,2,2-trifluoroethoxy)phenoxathiin-10,10-dioxide in the starting material that already is Form A. Typically, 3-fluoro-7-(2,2,2-trifluoroethoxy)phenoxathiin-10,10-dioxide is maintained in the slurry for 2 hours to 6 days, 6 hours to 2 days, or 10 to 24 hours.

In some embodiments in which Form A is prepared by taking up 3-fluoro-7-(2,2,2-trifluoroethoxy)phenoxathiin-10,10-dioxide into a slurry, a composition containing Form A of 3-fluoro-7-(2,2,2-trifluoroethoxy)phenoxathiin-10,10-dioxide is added to the slurry to facilitate formation of Form A. For purposes of the present method, "facilitate" formation of Form A refers to a shortening of the length of time for any particular amount or percentage of 3-fluoro-7-(2,2,2-trifluoroethoxy)phenoxathiin-10,10-dioxide to transition to Form A, or an increase in the total amount or percentage of 3-fluoro-7-(2,2,2-trifluoroethoxy)phenoxathiin-10,10-dioxide that ultimately transitions to Form A. The composition containing Form A that is added to a slurry can be at least about 10-99.9%, for example, at least about 10%, 20%, 30%, 40%, 50%, 60%, 70%, 80%, 90%, 95%, 96%, 97%, 98%, 99%, 99.5%, or 99.9% Form A.

Figure 3:
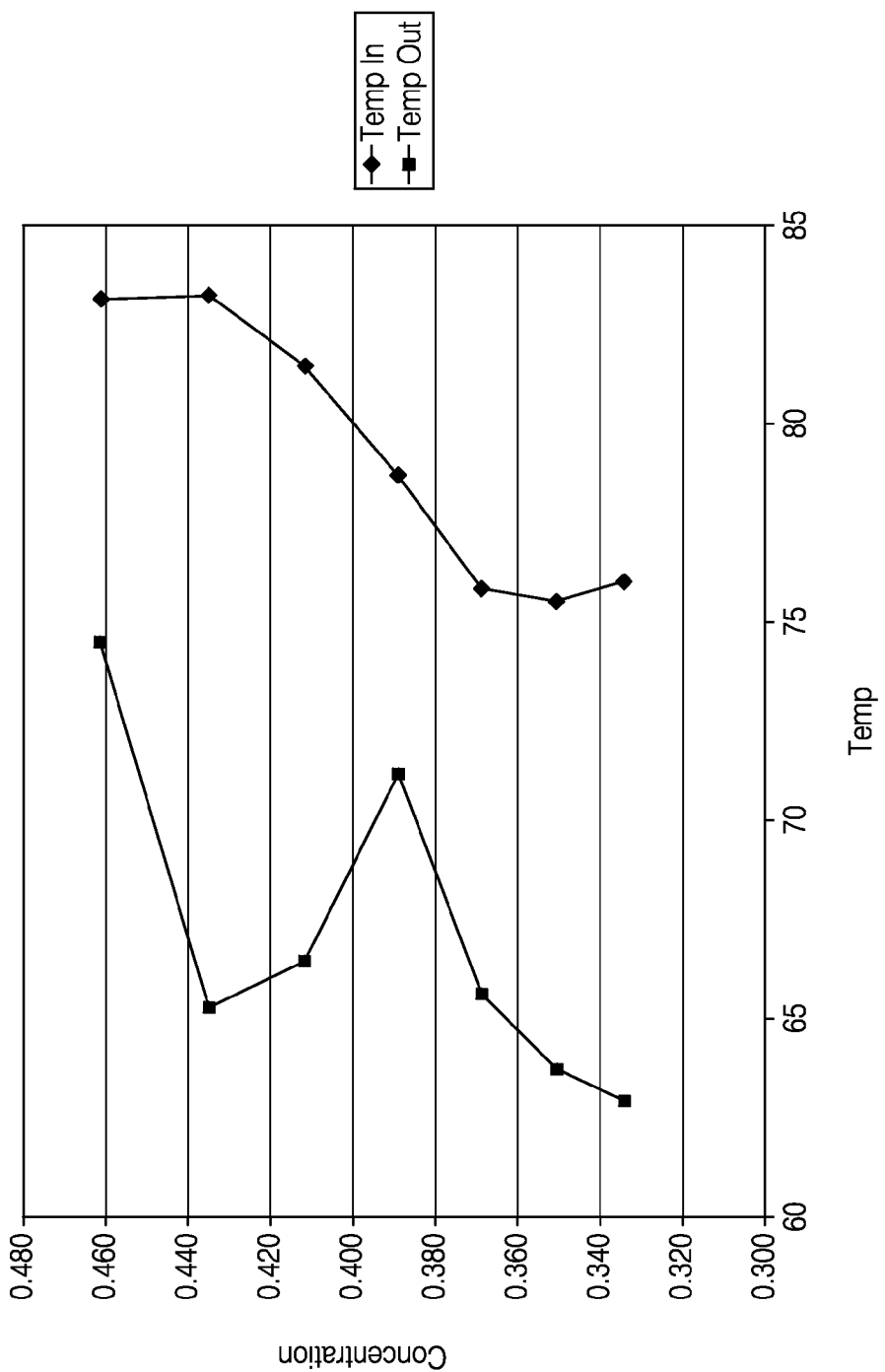
FIG. 3 depicts the temperature at which Form A of 3-fluoro-7-(2,2,2-trifluoroethoxy)phenoxathin 10,10-dioxide dissolves in (Temp In) a solution of acetic acid/10% $H_2O$ as a function of concentration of 3-fluoro-7-(2,2,2-trifluoroethoxy)phenoxathin 10,10-dioxide (upon dissolution), and the temperature at which 3-fluoro-7-(2,2,2-trifluoroethoxy) phenoxathin 10,10-dioxide precipitates out (Temp Out) from a solution of acetic acid/10% $H_2O$ as a function of concentration of 3-fluoro-7-(2,2,2-trifluoroethoxy)phenoxathin 10,10-dioxide.

In some embodiments, Form A can be prepared by precipitating 3-fluoro-7-(2,2,2-trifluoroethoxy)phenoxathiin-10,10-dioxide from solution. In such embodiments, 3-fluoro-7-(2,2,2-trifluoroethoxy)phenoxathiin-10,10-dioxide can be prepared by any method known in the art and need not have any Form A present in the 3-fluoro-7-(2,2,2-trifluoroethoxy)phenoxathiin-10,10-dioxide prior to dissolving 3-fluoro-7-(2,2,2-trifluoroethoxy)phenoxathiin-10,10-dioxide into solvent. The solvent and conditions under which Form A is prepared by precipitation can be any solvent and condition in which 3-fluoro-7-(2,2,2-trifluoroethoxy)phenoxathiin-10,10-dioxide can be dissolved and then, by adding or removing solvent or altering conditions (e.g., cooling), 3-fluoro-7-(2,2,2-trifluoroethoxy)phenoxathiin-10,10-dioxide precipitates from solution. Any of a variety of solvents, cooling rates, and other parameters can be used in precipitating Form A from solution, as will be apparent to one skilled in the art, based on the teachings provided herein. The particular conditions in which 3-fluoro-7-(2,2,2-trifluoroethoxy)phenoxathiin-10,10-dioxide dissolves and/or precipitates can vary depending on concentration of 3-fluoro-7-(2,2,2-trifluoroethoxy)phenoxathiin-10,10-dioxide and based on the rate of altering conditions of the solution (e.g. cooling rate). For example, typically the slower the cooling rate, the higher the likelihood that Form A will be the major form present in the precipitate. In addition, the concentration of 3-fluoro-7-(2,2,2-trifluoroethoxy)phenoxathiin-10,10-dioxide in solution can influence the temperature at which 3-fluoro-7-(2,2,2-trifluoroethoxy)phenoxathiin-10,10-dioxide precipitates (see, e.g., FIG. 3). An exemplary solvent for such a method is a combination of $H_2O$ and acetic acid, typically at least about 50-95%, for example, at least about 50%, 60%, 70%, 80%, 90%, or 95% acetic acid. Additional liquids in which such a method can be performed include, but are not limited to methanol, ethanol, n-butanol, t-amyl alcohol, acetonitrile, methyl t-butyl ether, isopropylacetate, dichloromethane, choloroform, carbon tetrachloride, xylenes, dimethylacetamide, dimethylsulfoxide, cumene, isopropyl acetate, acetic acid, methyl ethyl ketone, and acetone. Exemplary conditions for dissolving and precipitating 3-fluoro-7-(2,2,2-trifluoroethoxy)phenoxathiin-10,10-dioxide in $H_2O$ and acetate include temperatures of at least about 75° C.-125° C., for example, at least about 75° C., 80° C., 85° C., 90° C., 95° C., 100° C., 105° C., 110° C., 115° C., 120° C. or 125° C. for dissolving 3-fluoro-7-(2,2,2-trifluoroethoxy)phenoxathiin-10,10-dioxide in solution, and no more than about 75° C.-30° C., for example, no more than about 75° C., 70° C., 65° C., 60° C., 55° C., 40° C., 35° C. or 30° C. for precipitating 3-fluoro-7-(2,2,2-trifluoroethoxy)phenoxathiin-10,10-dioxide. In exemplary methods, the solvent content is unchanged and the temperature is decreased at a rate of at least about 5-40° C./hour, for example, at least about 5° C./hour, 10° C./hour, 15° C./hour, 20° C./hour, 25° C./hour, 30° C./hour, 35° C./hour, or 40° C./hour, or at a rate of no more than about 10-50° C./hour, for example, no more than about 10° C./hour, 15° C./hour, 20° C./hour, 25° C./hour, 30° C./hour, 35° C./hour, 40° C./hour, 45° C./hour or 50° C./hour.

In some embodiments in which 3-fluoro-7-(2,2,2-trifluoroethoxy)phenoxathiin-10,10-dioxide is precipitated from solution to prepare Form A, a solid composition containing Form A of 3-fluoro-7-(2,2,2-trifluoroethoxy)phenoxathiin-10,10-dioxide is added to the solution to facilitate formation of Form A. For purposes of the present method, "facilitate" formation of Form A refers to a shortening of the length of time for any particular amount or percentage of 3-fluoro-7-(2,2,2-trifluoroethoxy)phenoxathiin-10,10-dioxide to precipitate as Form A, or an increase in the total amount or percentage of 3-fluoro-7-(2,2,2-trifluoroethoxy)phenoxathiin-10,10-dioxide that ultimately precipitates as Form A, relative to the time, amount or percentage that forms in the absence of such a solid composition of Form A. The solid composition containing Form A that is added to such a solution can be at least about 10-99.9%, for example, at least about 10%, 20%, 30%, 40%, 50%, 60%, 70%, 80%, 90%, 95%, 96%, 97%, 98%, 99%, 99.5%, or 99.9% Form A. Typically, only Form A is present in detectable amounts in the solid composition containing Form A. The composition containing Form A is typically added under a condition in which not all of the added solid composition is dissolved subsequent to adding to the solution, and under a condition under which little or no (e.g. 1% or less, preferably no detectable amount) 3-fluoro-7-(2,2,2-trifluoroethoxy)phenoxathiin-10,10-dioxide dissolved in solution has already precipitated prior to addition of the solid composition containing Form A. Exemplary methods of precipitating 3-fluoro-7-(2,2,2-trifluoroethoxy)phenoxathiin-10,10-dioxide as Form A can be referred to as "seeding" methods, and can be performed in accordance with any of a variety of modifications of seeding methods that are generally known in the art. In one exemplary method, 5 g of 3-fluoro-7-(2,2,2-trifluoroethoxy)phenoxathiin-10,10-dioxide is placed in 12 volumes (60 mL) glacial acetic acid and heated to 117° C. or until solution is clear, and the temperature is held at this temperature for about 10-15 minutes. The hot solution is filtered using Whatman Number 3 filter paper (or equivalent) into a preheated vessel. The temperature is adjusted to 100° C., and a volume of water (pre-heated to 80° C.) is slowly added to generate a 10% $H_2O$ solution. The solution is warmed and held at 105° C. to ensure dissolution. The solution is then cooled at 20° C./hr to 75° C., and 0.5% wt of solid Form A is added as a slurry in acetic acid 10% water. The solution is then cooled at a rate of 20° C./hr and then filtered once the temperature reaches ambient temperature. The solid is filtered and dried in vacuo at 50° C.

Other methods known in the art for precipitating compounds from solution also can be used for preparing Form A of 3-fluoro-7-(2,2,2-trifluoroethoxy)phenoxathiin-10,10-dioxide. Such methods include, but are not limited to, vapor diffusion crystallization, and anti-solvent mediated crystallization. Anti-solvents that can be used in preparing Form A of 3-fluoro-7-(2,2,2-trifluoroethoxy)phenoxathiin-10,10-dioxide include, but are not limited to, $H_2O$, heptane and cyclohexane. Typically, heptane or cyclohexane is used as the anti-solvent for preparing Form A of 3-fluoro-7-(2,2,2-trifluoroethoxy)phenoxathiin-10,10-dioxide.

In addition to the methods provided above for preparing Form A of 3-fluoro-7-(2,2,2-trifluoroethoxy)phenoxathiin-10,10-dioxide, other methods known in the art for altering the polymorphic form of a compound can be used in a manner consistent with the teachings provided herein to prepare Form A of 3-fluoro-7-(2,2,2-trifluoroethoxy)phenoxathiin-10,10-dioxide. For example, Form A of 3-fluoro-7-(2,2,2-trifluoroethoxy)phenoxathiin-10,10-dioxide can be prepared by applying a high pressure load, e.g. at least about 20,000 pound load, to Form B of 3-fluoro-7-(2,2,2-trifluoroethoxy)phenoxathiin-10,10-dioxide for approximately 5 minutes or more.

Methods of Use

The compounds, compositions and formulations provided herein can be used in methods of treating medical, psychiatric and/or neurological conditions or disorders. In one embodiment, the methods include administering a MAO-inhibiting effective amount of Form A of 3-fluoro-7-(2,2,2-trifluoroethoxy)phenoxathiin-10,10-dioxide to a mammal, particularly a human, for the treatment of medical, psychiatric and/or neurological conditions and disorders such as, but not limited to, depressive disorders (major depressive disorder, dysthymia, childhood depression, atypical depression, bipolar disorder, mania and hypomania), anxiety disorders (generalized anxiety disorder, social anxiety disorder, phobias, obsessive compulsive disorder, panic disorder, post-traumatic stress disorder), premenstrual dysphoric disorder (also known as pre-menstrual syndrome), attention deficit disorder (with and without hyperactivity), Intermittent Explosive Disorder, Alzheimer's disease, Parkinson's disease, hyperactivity, conduct disorder, narcolepsy, obesity, eating disorders such as anorexia nervosa and bulimia nervosa, drug withdrawal syndromes and drug dependence disorders, including dependence from alcohol, opioids, amphetamines, cocaine, tobacco, and cannabis (marijuana), melancholia, panic disorder, anergic depression, treatment-resistant depression, headache, generalized anxiety disorder, acute and chronic pain syndromes, as exemplified by fibromyalgia, chronic low back pain, trigeminal neuralgia, visceral pain syndromes, such as irritable bowel syndrome, noncardiac chest pain, functional dyspepsia, interstitial cystitis, essential vulvodynia, urethral syndrome, orchialgia, temperomandibular disorder, atypical face pain, migraine headache, and tension headache; functional somatic disorders, for example, chronic fatigue syndrome, and other conditions in which alteration of MAO activity could be of therapeutic value.

In one embodiment, the compounds, compositions and formulations provided herein can be used in methods of treating depression states in which the compounds are particularly useful are those defined in the Diagnostic and Statistical Manual of Mental Disorders, third edition (DSM III), American Psychiatric Association, Washington, D.C. (1980), (DSM III, 296.2X to 296.6X and 301.13), including that characterized by anxiety or obsessional neuroses (DSM III, 300.40), or atypical depression including depression in the elderly or symptoms of early senility, especially symptoms relating to sociability and quality of life (DSM III, 296.70 and 296.82), e.g. accompanied by a personality disorder.

Other therapeutic uses for the compounds, compositions and formulations provided herein include treatment of post-traumatic stress disorder (DSM III, 300.30), anxiety states (DSM III, 300.00, 300.01, 300.02, 300.21, 300.22, 300.23 and 300.29), e.g. which are accompanied in an acute phase by panic attacks with or without phobia (DSM III 300.21), phobia (DSM III 300.23 and 300.29), appetite disorders, e.g. bulimia (DSM III, 307.51) and anorexia (DSM III, 307.10), and borderline personality disorder (DSM III, 301.83). Still further therapeutic uses for the compounds include treatment of headaches, e.g. migraine, muscle contraction and mixed (i.e., combination of migraine and muscle contraction) headaches.

Thus, presently provided are methods for the treatment of mental disorders, in mammals such as humans, where the mental disorders include depression, anxiety, and other conditions enumerated herein or otherwise known in the art as responsive to inhibition of MAO-A which comprises administering to said mammal an effective treatment amount of 3-fluoro-7-(2,2,2-trifluoroethoxy)phenoxathiin-10,10-dioxide, particularly Form A of 3-fluoro-7-(2,2,2-trifluoroethoxy) phenoxathiin-10,10-dioxide.

As used herein, therapeutically effective amount of Form A of 3-fluoro-7-(2,2,2-trifluoroethoxy)phenoxathiin-10,10-dioxide is an amount effective to achieve the intended purpose. The therapeutically effective amount can depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

Pharmaceutical Compositions

In another aspect, the present disclosure relates to a pharmaceutical composition comprising one or more physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the instant compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the instant compounds in water-soluble form. Additionally, suspensions of the instant compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

For oral administration, the compounds can be formulated readily by combining the instant compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the instant compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of instant compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of instant compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the instant compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the instant compounds in water-soluble form, such as eyedrops, or in gellan gum (Shedden et al., *Clin. Ther.,* 23(3):440-50 (2001)) or hydrogels (Mayer et al., *Ophthalmologica,* 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The instant compounds may also be formulated in rectal compositions such as suppositories or retention enemas, e.g. containing conventional suppository bases such as cocoa butter or other glycerides.

In addition to the formulations described previously, the instant compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents that include the instant compounds intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The instant compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g. Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Exemplary methods for determining the MEC are provided in U.S. Pat. No. 6,110,961, which is incorporated by reference herein in its entirety.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

Exemplary methods for determining the efficacy and toxicity are provided in U.S. Pat. No. 6,110,961, which is incorporated by reference herein in its entirety. Briefly, MAO can be assayed with $^3$H serotonin (0.2 mM, 5 Ci/mole) and $^{14}$C β-phenethylamine (10 µM, 3 Ci/mole) as substrates in a double-label assay (see, e.g., White and Glassman, J. Neurochem. 29:987-97 (1977)). Under these conditions, serotonin can be selectively metabolized by MAO-A and β-phenethylamine by MAO-B. For studies of the kinetic mechanism of inhibition, this method is used except that a single substrate, serotonin or tyramine, can be varied over a 10-fold concentration range that included the $K_m$ concentration. When tyramine is used as substrate, the extract can be pretreated with deprenyl (1 µM) to inhibit all MAO-B activity. MAO-A activity can be determined in the absence and presence of the compound under test at each substrate concentration in duplicate or triplicate assays.

In another exemplary method, the compound can be tested for effects on the pressor response induced by orally administered tyramine in a conscious, unrestrained rat model. The method involves direct measurement of mean arterial blood pressure from a cannula implanted in a carotid artery and exteriorized through a small incision in the back of the neck. Peak changes in the pressor response following tyramine (p.o.) in animals pretreated with test compound (p.o.) can be compared with changes seen in animals pretreated with either the known MAO inhibitor, phenelzine, (p.o.) or vehicle (water) alone. To compare effects at equipotent doses that are relevant to antidepressant activity, either the test compound or phenelzine can be given in a single oral dose that produces approximately 80% inhibition of brain MAO-A by the time of tyramine administration 3 hours later.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

3-Fluoro-7-(2,2,2-trifluoroethoxy)phenoxathiin

Also provided herein is the compound 3-fluoro-7-(2,2,2-trifluoroethoxy)phenoxathiin or a solvate or a hydrate thereof, and methods of making and using 3-fluoro-7-(2,2,2-trifluoroethoxy)phenoxathiin or a solvate or a hydrate thereof. In some embodiments, the 3-fluoro-7-(2,2,2-trifluoroethoxy)phenoxathiin or solvate or hydrate thereof is provided in substantially pure form. As provided herein, 3-fluoro-7-(2,2,2-trifluoroethoxy)phenoxathiin-10,10-dioxide can be prepared, where the synthesis includes oxidizing 3-fluoro-7-(2,2,2-trifluoroethoxy)phenoxathiin to form 3-fluoro-7-(2,2,2-trifluoroethoxy)phenoxathiin-10,10-dioxide. Applicants have found that use of 3-fluoro-7-(2,2,2-trifluoroethoxy)phenoxathiin provides a particularly desirable path for the preparation of 3-fluoro-7-(2,2,2-trifluoroethoxy)phenoxathiin-10,10-dioxide since such synthetic route provides good yield and scalability. 3-Fluoro-7-(2,2,2-trifluoroethoxy)phenoxathiin also can find a particularly desirable use in synthetic methods that facilitate a high yield of Form A of 3-fluoro-7-(2,2,2-trifluoroethoxy)phenoxathiin-10,10-dioxide.

3-Fluoro-7-(2,2,2-trifluoroethoxy)phenoxathiin can be prepared according to the teachings provided herein and the knowledge in the art. Briefly, treating 5-(2,2,2-trifluoroethoxy)-2-mercaptophenol with base followed by addition of 1,4-difluoro-2-nitrobenzene can afford 3-fluoro-7-(2,2,2-trifluoroethoxy)phenoxathiin. For example, 5-(2,2,2-trifluoroethoxy)-2-mercaptophenol can be combined with potassium tert-butoxide followed by combination with 1,4-difluoro-2-nitrobenzene which upon heating can afford 3-fluoro-7-(2,2, 2-trifluoroethoxy)phenoxathiin. In an exemplary embodiment, the solvent used to dissolve potassium tert-butoxide and 1,4-difluoro-2-nitrobenzene can be anhydrous N,N-dimethylformamide. For example, 5-(2,2,2-trifluoroethoxy)-2-mercaptophenol dissolved in a THF/MTBE mixture can be added to potassium tert-butoxide in N,N-dimethylformamide; subsequent to their combination, under the conditions disclosed herein, the mixture can then be treated with 1,4-difluoro-2-nitrobenzene dissolved in N,N-dimethylformamide.

In some embodiments, the 5-(2,2,2-trifluoroethoxy)-2-mercaptophenol can be generated by hydrolysis of 6-(2,2,2-trifluoroethoxy)benzo[d][1,3]oxathiol-2-one and used in the aforementioned step without isolation in a solid form. In one embodiment, the 6-(2,2,2-trifluoroethoxy)benzo[d][1,3]oxathiol-2-one can be hydrolyzed with aqueous sodium hydroxide to afford 5-(2,2,2-trifluoroethoxy)-2-mercaptophenol. In an exemplary embodiment, the 6-(2,2,2-trifluoroethoxy) benzo[d][1,3]oxathiol-2-one dissolved in degassed THF can be hydrolyzed by addition of degassed aqueous sodium hydroxide; subsequently, the reaction can be quenched with acid and the resultant 5-(2,2,2-trifluoroethoxy)-2-mercaptophenol can be obtained in organic solution. In some aspects, the 5-(2,2,2-trifluoroethoxy)-2-mercaptophenol can be obtained in organic solution by partitioning the solvent mixture with degassed MTBE, extracting the remaining aqueous solution with degassed MTBE, and combining the organic layers containing 5-(2,2,2-trifluoroethoxy)-2-mercaptophenol. The 5-(2,2,2-trifluoroethoxy)-2-mercaptophenol dissolved in the organic solution (THF/MTBE) can be used directly in the ring forming reaction without isolation.

3-Fluoro-7-(2,2,2-trifluoroethoxy)phenoxathiin can be used to prepare 3-fluoro-7-(2,2,2-trifluoroethoxy)phenoxathiin-10,10-dioxide according to the teachings provided herein and the knowledge in the art. Briefly, 3-fluoro-7-(2,2, 2-trifluoroethoxy)phenoxathiin can be oxidized at the sulfur atom so as to yield 3-fluoro-7-(2,2,2-trifluoroethoxy)phenoxathiin-10,10-dioxide. Oxidation of 3-fluoro-7-(2,2,2-trifluoroethoxy)phenoxathiin can be performed using any of a variety of methods known in the art. For example, 3-fluoro-7-(2,2,2-trifluoroethoxy)phenoxathiin can be oxidized with oxone, dimethyldioxirane, peracetic acid and other oxidants known by those of skill in the art. In one embodiment, 3-fluoro-7-(2,2,2-trifluoroethoxy)phenoxathiin can be dissolved in acetic acid and then oxidized to the sulfone, 3-fluoro-7-(2,2,2-trifluoroethoxy)phenoxathiin-10,10-dioxide, by addition of peracetic acid; the 3-fluoro-7-(2,2,2-trifluoroethoxy)phenoxathiin-10,10-dioxide can then be isolated after quenching the excess oxidant with an aqueous solution of sodium sulfite. For example, 3-fluoro-7-(2,2,2-trifluoroethoxy)phenoxathiin-10,10-dioxide can be isolated from the aqueous solvent mixture by cooling below 25° C. and collecting the solid by filtration; the solid can be rinsed with water, and then dried under vacuum to afford the substantially dry desired pure target compound. Typically, the method of preparing 3-fluoro-7-(2,2,2-trifluoroethoxy)phenoxathiin-10,10-dioxide from 3-fluoro-7-(2,2,2-trifluoroethoxy)phenoxathiin is performed in a manner that yields 3-fluoro-7-(2,2,2-trifluoroethoxy)phenoxathiin-10,10-dioxide partially or completely in Form A.

The following examples are included for illustrative purposes only and are not intended to limit the scope of the invention.

EXAMPLES

Analytical Methods

The methods provided below were used generally for all Examples described herein

NMR

For each NMR analysis described herein, the assay was performed as essentially as follows. Acquisition of $^1$H NMR spectra was performed using 1-10 mg of sample dissolved in approximately 1 mL of CDCl₃. Spectra were acquired using a 300 MHZ Bruker AVANCE with 5 mm QNP probe at 300.13 MHz with 16 to 128 scans and a pulse delay of 1.0 s with a 30 degree pulse.

Acquisition of $^{13}C$ NMR spectra was performed using 1-10 mg of sample dissolved in approximately 1 mL of CDCl₃. Spectra were acquired using a 75 MHZ Bruker AVANCE with 5 mm QNP probe with proton decoupling at 75.47 MHz with 10000 to 16000 scans and a pulse delay of 0.5 s with a 30 degree pulse width.

Acquisition of $^{19}F$ NMR spectra was performed using 1-10 mg of sample dissolved in approximately 1 mL of CDCl₃. Spectra were acquired using a 282 MHZ Bruker AVANCE with 5 mm QNP probe at 282.37 MHz with or without proton decoupling with 1 to 200 scans and a pulse delay of 1.0 s with a 90 degree pulse width.

The measured $^1H$, $^{19}F$, and $^{13}C$ NMR peaks of the intermediate compounds of the syntheses described below were consistent with theoretical peaks predicted based on the atomic structure.

HPLC

For each HPLC analysis described herein, the assay was performed as essentially as follows. Approximately 12.0 mg of sample was weighed into a 200-mL volumetric flask. 100 ml of acetonitrile with 1.0% TFA was utilized to dissolve the sample with the use of sonication as necessary. Once the sample has dissolved, the solution is diluted to volume with water and mixed thoroughly.

HPLC Instrument Conditions

| Column: | Waters SunFire C18, 3.5 μm, 4.6 × 150 mm |
|---|---|
| Column Temperature: | Ambient |
| Detection: | 220 nm |
| Mobile Phase A: | Water with 0.05% TFA |
| Mobile Phase B: | Acetonitrile with 0.04% TFA |
| Gradient: | See Table below |
| Flow Rate: | 1.0 mL/minute |
| Injection Volume: | 10 μL |
| Data Collection Time: | 20 minutes |
| Total Analysis Time: | 30 minutes |
| Needle/Seal Wash: | 50% Acetonitrile/50% Water/0.5% TFA |
| Sample Concentration: | 12 mg/200 mL (0.06 mg/mL) |

Gradient Conditions

| Time (minutes) | % A | % B |
|---|---|---|
| 0.0 | 95 | 5 |
| 10 | 5 | 95 |
| 20 | 5 | 95 |
| 21 | 95 | 5 |
| 30 | 95 | 5 |

DSC

For each Differential Scanning Calorimetry (DSC) or melting point measurement described herein, the analysis was performed using a Mettler 822$^e$ Differential Scanning Calorimeter. Samples were weighed in an aluminum pan, covered with a pierced lid, and then crimped. Analysis conditions were 30° C. to 300-500° C. ramped at 10° C./min.

FTIR

For each Fourier Transform Infrared measurement described herein, the analysis was performed using an attenuated total reflection (ATR) attachment on a Thermo Nicolet Avatar 370 Spectrometer. After a background of ambient lab conditions was obtained, samples were placed on ATR, compressed with an anvil, and the spectrum acquired.

Example 1

This example describes the synthesis of 3-fluoro-7-(2,2,2-trifluoroethoxy)phenoxathiin-10,10-dioxide which yielded primarily Form A of 3-fluoro-7-(2,2,2-trifluoroethoxy)phenoxathiin-10,10-dioxide.

Step 1—Synthesis of the Compound Having Formula I

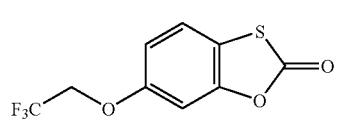

Formula I

6-Hydroxy-1,3-benzoxathiol-2-one (700.0 g, 4.16 mol) and anhydrous N,N-dimethylformamide (6.8 L) were combined and stirred under nitrogen. To the resulting solution was added 2,2,2-trifluoroethyl trifluoromethanesulfonate (966.1 g, 4.16 mol) in one portion (exotherm from 16.9° C. to 17.5° C.). The batch temperature was equilibrated over 5 min. (18.2° C.), and the flask originally containing the 2,2,2-trifluoroethyl trifluoromethanesulfonate was rinsed with DMF (0.2 L) and the rinse added to the batch. Anhydrous potassium carbonate (1.15 kg, 8.32 mol) was added in one portion. An exotherm was noted (batch temperature rose from 18.2° C. to 26.6° C. over 2 h) and the reaction was monitored via HPLC. After 6.5 h, the reaction mixture was filtered through a Buchner filter and the filtrate was collected. The solids were rinsed with DMF (0.7 L, ACS grade). The filtrate was acidified by the addition of glacial acetic acid (26 mL) to pH=5. Purified water (7 L) was added to the 10-L carboy as a rinse and the water was transferred rapidly to the batch (exotherm from 27° C. to 37° C.). The resulting slurry was stirred for 20 min at 36-37° C. The solids were filtered into a Buchner filter and the filtrate was collected. The solids were rinsed with water (2×3 L), transferred in two drying trays (1178.7 g, KF=21.7%) and dried under vacuum at room temperature for 16 h (1033.9 g) and continued drying for 23 h at 40-45° C. to yield intermediate compound having Formula I as a white solid (845.8 g, 81% yield).

HPLC analysis was performed on the intermediate compound having Formula I. Results from HPLC analysis of the intermediate compound having Formula I was as follows: 98.9% (AUC), $t_R$=11.5 min. $^1H$, $^{19}F$, and $^{13}C$ NMR analysis was consistent with the intermediate compound having Formula I ($^1H$ NMR (CDCl₃, 300 MHz, ppm): 7.33 (d, J=8.5 Hz, 1H), 6.94 (d, J=2.5 Hz, 1H), 6.89 (dd, J=2.5 and 8.5 Hz, 1H), 4.38 (q, J=8.0 Hz, 2H); $^{13}C$ NMR (CDCl₃, 75 MHz, ppm): 169.3, 157.6, 149.2, 128.9, 125.2, 123.4, 121.5, 117.8, 116.5, 113.0, 100.4, 67.4, 66.9, 66.5, 66.0; $^{19}F$ (CDCl₃, 282 MHz, ppm): −74.2). Solvent content determined by the Karl Fischer method of the intermediate compound having Formula I was 0.17 wt % H₂O.

Step 2—Synthesis of the Compound Having Formula Iv

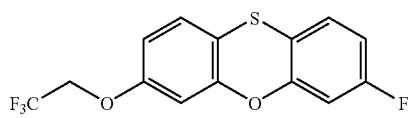

Formula IV

A compound of Formula I [810.0 g, 3.23 mol] and tetrahydrofuran (degassed, 1.6 L) were combined with stirring under nitrogen and maintained in an ambient water bath. Degassed sodium hydroxide (2 N, 4.8 L) was added in one portion (exotherm from 13.7° C. to 42.0° C.) and the mixture was stirred while the batch was maintained in the ambient temperature water bath. After 45 min, the reaction mixture was cooled to 10° C. and concentrated hydrochloric acid (0.89 L) was slowly added at such a rate that the reaction temperature remained below 20° C. The addition took 20 min and the pH was checked to be pH=1. Methyl tert-butyl ether (MTBE; degassed, 1.6 L) was added and the mixture was stirred for 5 min. The layers of the biphasic mixture were separated. The aqueous layer was re-extracted with MTBE (degassed, 1.6 L). The organic layers were combined (KF=4.17 wt % H₂O), dried over MgSO₄ (243 g), filtered, and the filtrate was collected. The solids were rinsed with fresh MTBE (degassed, 0.4 L) and the rinse was added to the filtrate. The filtrate was flushed with nitrogen and capped to afford intermediate compound having Formula II as a yellow solution in MTBE/THF (HPLC 84.8% (AUC), $t_R$=to 10.5 min). Solvent content determined by the Karl Fischer method was 2.47 wt % H₂O.

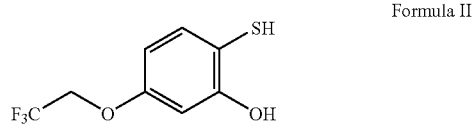

Formula II

In a separate reaction, potassium tert-butoxide (726.5 g, 6.47 mol) and anhydrous N,N-dimethylformamide (3.63 L) were combined and stirred under nitrogen. The mixture was stirred until a clear solution was formed and the solution was cooled to 5° C. in an ice bath. The solution of intermediate compound having Formula II in THF/MTBE from above [theoretical 3.23 mol] was slowly added to the reaction mixture over 45 min such that the reaction temperature remained below 15° C. During the addition, the reaction mixture became very viscous and a thick, yellow slurry formed. More rapid stirring allowed the slurry to stir freely. The mixture was stirred below 15° C. for 5 min and a solution of the compound having Formula III (463.5 g, 2.91 mol) in anhydrous N,N-dimethylformamide (0.93 L) was slowly added to the reaction mixture over 25 min such that the reaction temperature remained below 15° C. The resulting brown solution was stirred at 15° C. for 30 min and HPLC analysis showed no remaining compound having Formula III.

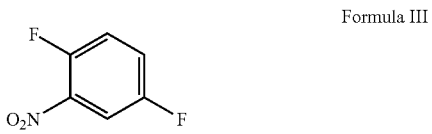

Formula III

The reaction was heated to 130° C. with a heating ramp set at 50° C./h. At about 66° C., solvent was distilled out of the reaction mixture (about 1 L) while the heating continued. The mixture took 4.5 h to reach 130° C. After 3.5 h at 130° C., the mixture was cooled to 30° C. The reaction mixture was added to water (8.1 L, cooled in an ice bath) over 5 min. The resulting slurry was stirred and was cooled to below 20° C. in an ice bath, stirred for 20 min, and the solids were filtered through two Buchner filters. The wet solids from the two filters were combined and homogenized and filtered again. The solids were rinsed with water (2×1.6 L) and transferred to two drying trays (1600 g), and dried under vacuum at 25° C. for 10.5 h. Karl Fischer analysis showed a water content of about 40 wt % water, and drying was continued at 50° C. for 16 h to yield crude intermediate compound having Formula IV as a brown solid [890.5 g]: HPLC 84.9% (AUC), $t_R$=14.2 min the ¹H NMR spectrum was consistent with the assigned structure. Solvent content determined by the Karl Fischer method was 0.20 wt % H₂O.

Formula IV [889.2 g] and 2-propanol (4.43 L) were combined with stirring under nitrogen. The slurry was heated to 65° C. over 40 min. The temperature was maintained at 65° C. for 20 min and the solution was cooled slowly to 43° C. over 50 min (crystallization occurred at 55° C.). The mixture was then cooled more rapidly with a water bath, then an ice bath below 10° C. over 25 min. The slurry was stirred for 50 min below 10° C. The solids were filtered through a Buchner filter. The solids were rinsed with cold 2-propanol (0.8 L), followed by 50% water/2-propanol (2×0.8 L). The wet solid filtrates were transferred to two drying trays (1064 g) and dried under vacuum at 50° C. for 17.5 h to yield pure compound having Formula IV as a tan solid [569.1 g, 61% yield vs compound having Formula III]: HPLC 99.6% (AUC), $t_R$=14.1 min. The ¹H NMR, ¹³C NMR, and ¹⁹F NMR spectra were consistent with the assigned structure (¹H NMR (CDCl₃, 300 MHz, ppm): 7.00-7.06 (m, 2H), 6.73-6.80 (m, 2H), 6.64-6.68 (m, 2H), 4.32 (q, J=8.0 Hz, 2H); ¹³C NMR (CDCl₃, 75 MHz, ppm): 162.8, 159.5, 156.3, 151.7, 151.5, 126.3, 126.2, 123.9, 120.2, 114.2, 112.9, 111.0, 110.7, 105.1, 104.8, 104.3, 65.8, 65.3, 64.8, 64.4; ¹⁹F (CDCl₃, 282 MHz, ppm): −74.3, −114.2). Solvent content determined by the Karl Fischer method was 0.17 wt % H₂O.

Figure 4:
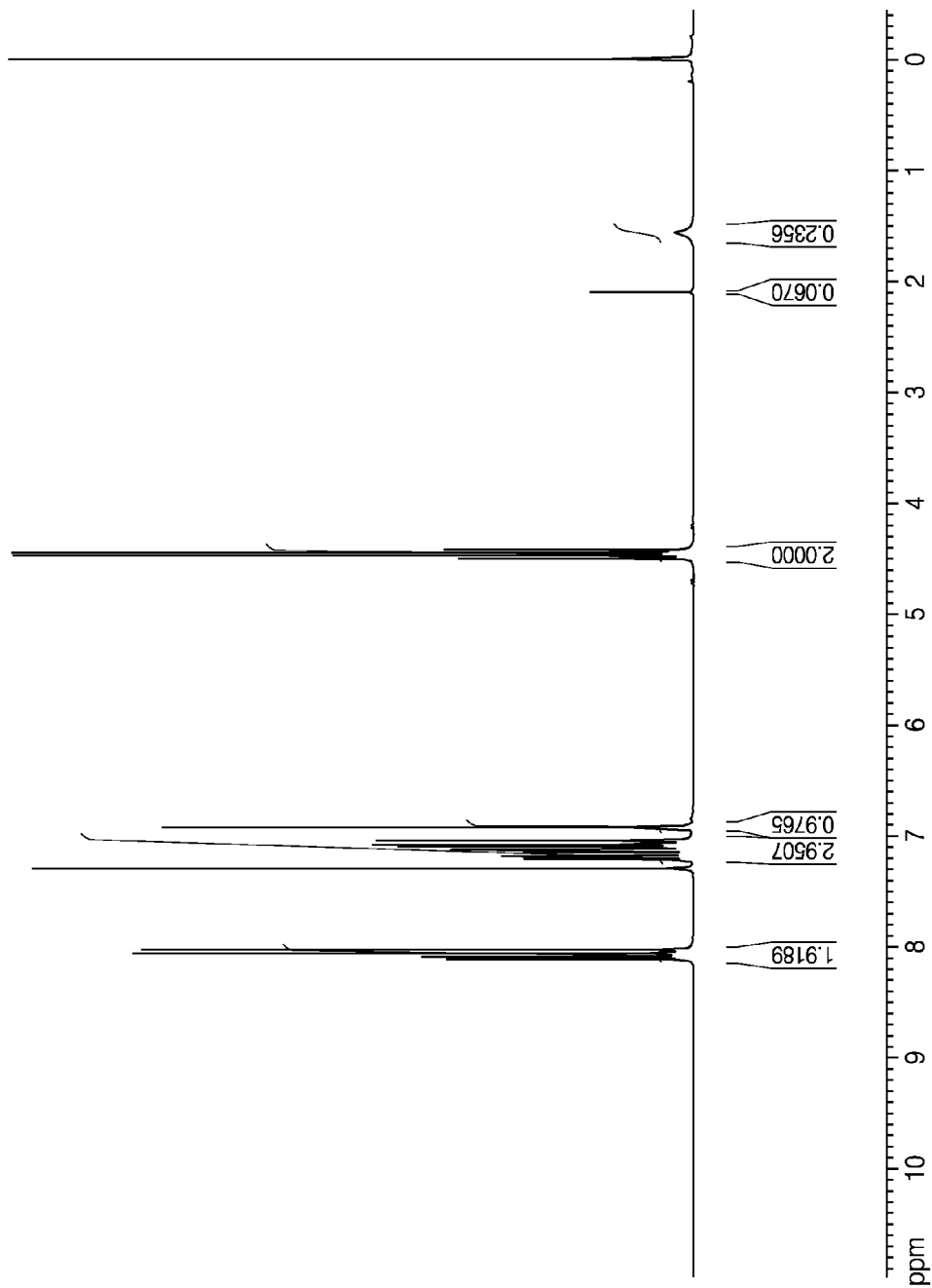
FIG. 4 depicts the $^1H$ NMR solution spectrum of 3-fluoro-7-(2,2,2-trifluoroethoxy)phenoxathiin-10,10-dioxide as prepared in Example 1.
Figure 5:
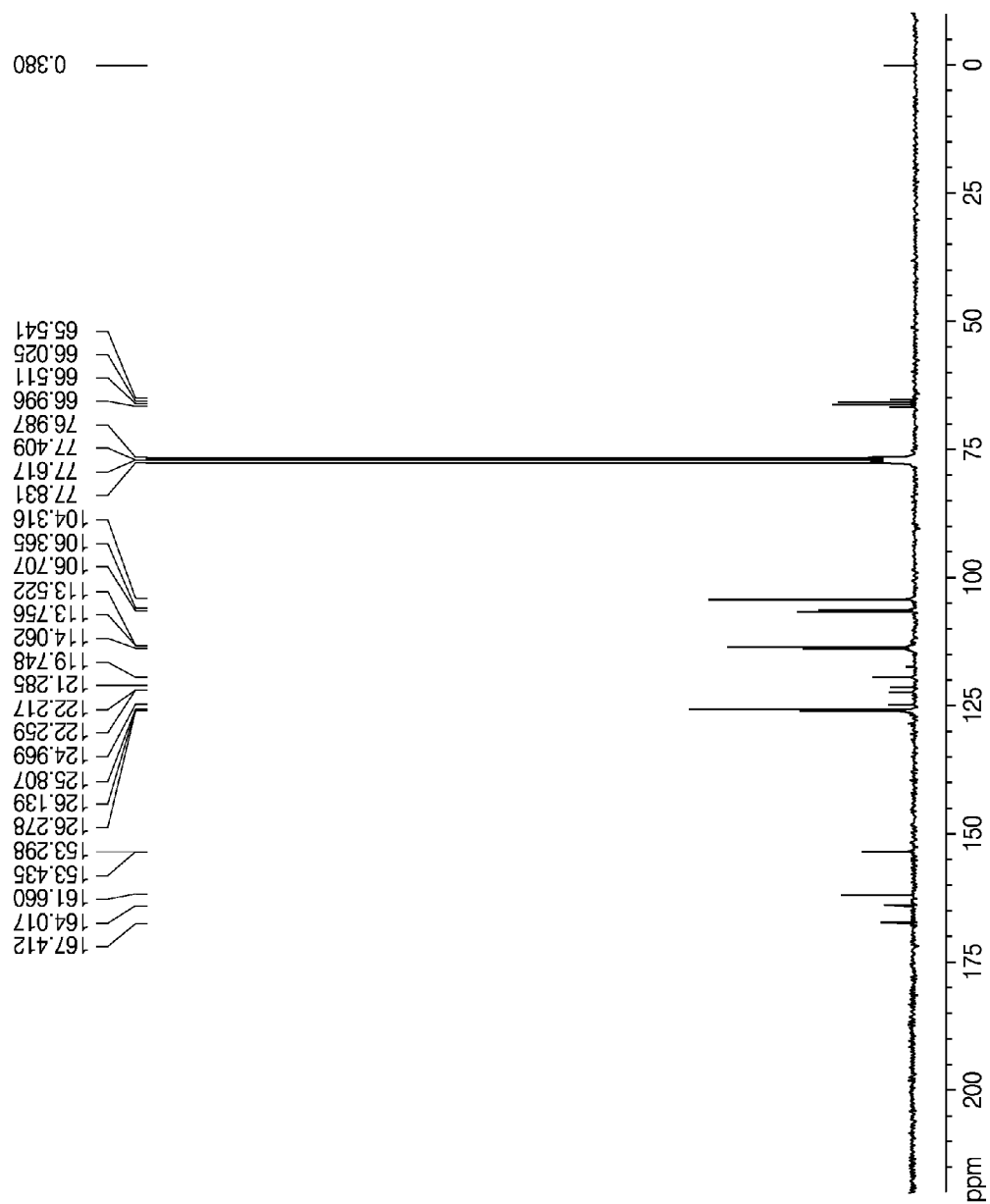
FIG. 5 depicts the $^{13}C$ NMR solution spectrum of 3-fluoro-7-(2,2,2-trifluoroethoxy)phenoxathiin-10,10-dioxide as prepared in Example 1.
Figure 6:
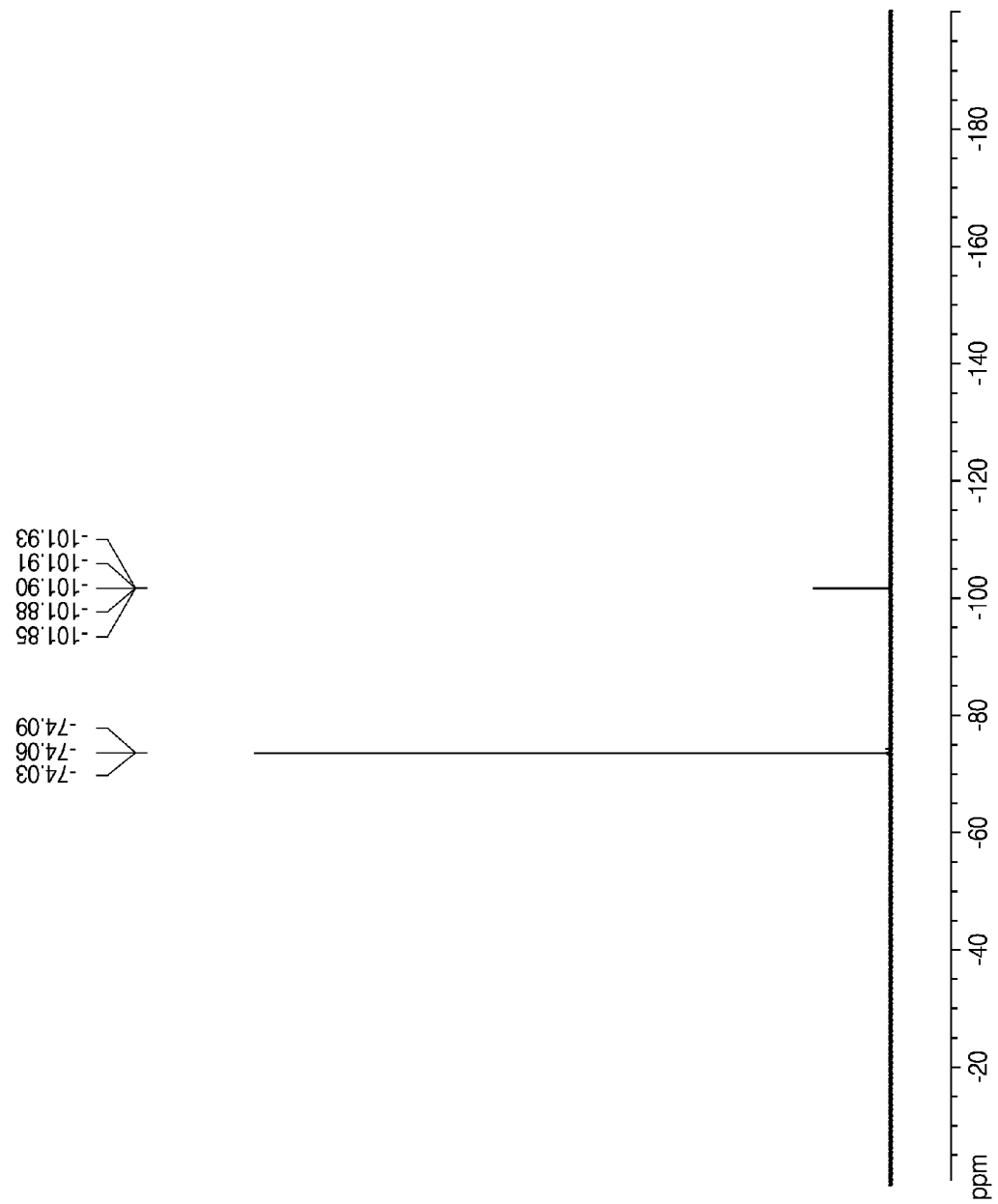
FIG. 6 depicts the $^{19}F$ NMR solution spectrum of 3-fluoro-7-(2,2,2-trifluoroethoxy)phenoxathiin-10,10-dioxide as prepared in Example 1.

Step 3—Synthesis of 3-fluoro-7-(2,2,2-trifluoroethoxy)phenoxathiin-10,10-dioxide Formula IV [562.8 g, 1.78 mol] from above and glacial acetic acid (8.4 L) were combined with stirring under nitrogen (endotherm: ambient to 14.8° C.). Peracetic acid (35 wt % in acetic acid, 342 mL, 1.78 mol) was diluted with glacial acetic acid (342 mL) The resultant solution was slowly added to the mixture while cooling in an ice bath. This peracetic acid solution was added to the reaction mixture over 30 min at a rate such that the temperature remained below 20° C. The reaction mixture was stirred for 25 min, then peracetic acid (35 wt %, 346 mL, 1.95 mol) was added to the reaction mixture over 5 min, keeping the reaction temperature below 20° C. After 10 min, the mixture was heated to 40° C. over 1 h and monitored by HPLC analysis. The temperature rose to a maximum of 50° C. After 5.5 h, additional peracetic acid (35 wt %, 0.2 equiv) was added and the reaction continued. After 7 h, the mixture had partially precipitated, and the mixture was cooled to 33° C. Water (4 L) was added to the batch and the mixture continued cooling to 22° C. An aqueous solution of sodium sulfite (1 equiv of sodium sulfite in 3 L of water) was added over 15 min at a rate such that the reaction temperature remained below 25° C. The presence of unreacted peracetic acid was noted (by potassium iodide test paper) and additional sodium sulfite was added (0.35 equiv of sodium sulfite in 0.5 L of water) over 10 min such that the reaction temperature remained below 25° C. The resulting light orange slurry was stirred below 25° C. for 15 min and filtered, and the filtrate collected. The solids were rinsed with water (2×2.8 L). The wet solids (1034.6 g) were transferred to two drying trays and dried under vacuum at 50° C. for 13 h to afford pure 3-fluoro-7-(2,2,2-trifluoroethoxy)phenoxathiin-10,10-dioxide as a white solid [599.2 g, 96% yield]: HPLC 99.6% (AUC), $t_R$=11.6 min. $^1$H NMR, $^{13}$C NMR, and $^{19}$F NMR (see FIGS. 4-6) were consistent with the structure of 3-fluoro-7-(2,2,2-trifluoroethoxy)phenoxathiin-10,10-dioxide ($^1$H NMR (CDCl$_3$, 300 MHz, ppm): 7.99-8.08 (m, 2H), 7.01-7.18 (m, 3H), 6.89 (d, J=2.5 Hz, 1H), 4.45 (q, J=8.0 Hz, 2H); $^{13}$C NMR (CDCl$_3$, 75 MHz, ppm): 167.4, 164.0, 161.6, 153.4, 153.3, 126.3, 126.1, 125.8, 124.9, 122.2, 122.2, 121.3, 119.7, 114.0, 113.7, 113.5, 106.7, 106.3, 104.3, 67.0, 66.5, 66.0, 65.5; $^{19}$F (CDCl$_3$, 282 MHz, ppm): −74.0, −101.9). Solvent content determined by the Karl Fischer method was 0.02 wt % H$_2$O.

Example 2

This example describes the synthesis of 3-fluoro-7-(2,2,2-trifluoroethoxy)phenoxathiin-10,10-dioxide which yielded Form B of 3-fluoro-7-(2,2,2-trifluoroethoxy)phenoxathiin-10,10-dioxide. Compounds having Formulas I-IV are the same as in Example 1.

Step 1—Synthesis of the Compound Having Formula I

6-Hydroxy-1,3-benzoxathiol-2-one (700.0 g, 4.16 mol) and anhydrous N,N-dimethylformamide (6.8 L) were combined and stirred under nitrogen. To the resulting solution was added 2,2,2-trifluoroethyl trifluoromethanesulfonate (966.1 g, 4.16 mol) in one portion (exotherm from 19.4° C. to 20.4° C.) and anhydrous potassium carbonate (1.15 kg, 8.32 mol) in one portion. An exotherm was noted (batch temperature rose from 20.4° C. to 24.6° C. over 2 h) and the reaction was monitored via HPLC. After 5 h, the reaction mixture was filtered through a Buchner filter, and the filtrate was collected. The solids were rinsed with DMF (0.7 L, ACS grade). The filtrate was acidified by the addition of glacial acetic acid (26 mL) to pH=5. Purified water (7 L) was added as a rinse and the water was transferred rapidly to the batch (exotherm from 27° C. to 37° C.). The resulting slurry was stirred for 20 min at 35° C. The solids were filtered through a Buchner filter and the filtrate was collected. The solids were rinsed with water (2×3 L), transferred in two drying trays (1196.54 g, solvent content determined by the Karl Fischer method was 19.6 wt % H$_2$O) and dried under vacuum at 30° C. for 15.5 h (943.5 g) and continued drying for 22 h at 35° C. to afford intermediate compound having Formula I as a white solid [910.5 g, 87% yield]: HPLC 98.2% (AUC), $t_R$=11.4 min; the $^1$H, $^{19}$F and $^{13}$C NMR spectra were consistent with the assigned structure ($^1$H NMR (CDCl$_3$, 300 MHz, ppm): 7.33 (d, J=8.5 Hz, 1H), 6.94 (d, J=2.5 Hz, 1H), 6.89 (dd, J=2.5 and 8.5 Hz, 1H), 4.38 (q, J=8.0 Hz, 2H); $^{13}$C NMR (CDCl$_3$, 75 MHz, ppm): 169.3, 157.6, 149.2, 128.9, 125.2, 123.4, 121.5, 117.8, 116.5, 113.0, 100.4, 67.4, 66.9, 66.5, 66.0; $^{19}$F (CDCl$_3$, 282 MHz, ppm): −74.2). Solvent content determined by the Karl Fischer method was 0.25 wt % H$_2$O.

Step 2—Synthesis of the Compound Having Formula IV

Intermediate compound having Formula I [810.0 g, 3.23 mol] and tetrahydrofuran (degassed, 1.6 L) were combined under nitrogen and maintained in an ambient bath. Degassed sodium hydroxide [2 N, 4.8 L] was added in one portion (exotherm from 13.8° C. to 37.6° C.) and the mixture was stirred while the batch was maintained in the ambient temperature water bath. After 45 min, the reaction mixture was cooled to 10° C. and concentrated hydrochloric acid (0.89 L) was slowly added at such a rate that the reaction temperature remained below 20° C. The addition took 10 min and the batch had a pH=1. MTBE (degassed, 1.6 L) was added and the mixture was stirred for 5 min. The layers of the biphasic mixture were separated. The aqueous layer was re-extracted with MTBE (degassed, 1.6 L). The organic layers were combined (solvent content determined by the Karl Fischer method was 3.7 wt % H$_2$O), dried over MgSO$_4$ (243 g), filtered, and the filtrate was collected. The solids were rinsed with fresh MTBE (degassed, 0.4 L) and the rinse was added to the filtrate. The filtrate was flushed with nitrogen and capped to afford intermediate compound having Formula II as a yellow solution in MTBE/THF: HPLC 93.4% (AUC), $t_R$=10.5 min. Solvent content determined by the Karl Fischer method was 2.5 wt % H$_2$O.

In a separate reaction, potassium tert-butoxide (727.1 g, 6.48 mol) and anhydrous 1-methyl-2-pyrrolidinone (3.63 L) were combined and stirred under nitrogen. The mixture was stirred until a clear solution was formed and the solution was cooled to 5° C. in an ice bath. The solution of intermediate compound having Formula II in THF/MTBE from above was slowly added to the reaction mixture over 35 min such that the reaction temperature remained below 15° C. The compound having Formula III (463.9 g, 2.91 mol) was mixed with anhydrous 1-methyl-2-pyrrolidinone (0.93 L), and the solution was slowly added to the reaction mixture containing the compound having Formula II over 17 min such that the reaction temperature remained below 15° C. The resulting brown solution was stirred at 15° C. for 30 min and HPLC analysis showed no remaining compound having Formula III. The reaction was heated to 25° C. and solvent was distilled under vacuum (10 in. Hg). After 30 min, no distillate was collected. The reaction temperature was increased to 35° C. and 15 in. Hg for 2 h and the distillate collected (about 300 mL). When no more vapors condensed, the reaction was heated to 105° C. at a rate of 50° C./h. At 85° C., solvent was distilled out of the reaction mixture (about 1 L) while heating continued to 105° C. After 3.5 h at 105° C., the mixture was cooled to 30° C.

The reaction mixture was added to 8.1 L of cooled water via vacuum transfer over 5 min. The resulting slurry was cooled to below 20° C. in an ice bath and stirred for 20 min. The concentration of the resulting compound having Formula IV was 0.34 mg/mL. The slurry was stirred for an additional 30 min, and the concentration of compound having Formula IV was still 0.34 mg/mL. The solids were filtered, rinsed with water (2×1.6 L), and dried under vacuum at 25° C. for 12 h. Karl Fischer analysis showed a water content of about 29 wt % water [1292 g]: HPLC 81.6% (AUC), $t_R$=14.2 min.

To the still-wet solids were added 2-propanol (7.2 L) and water (1.4 L) to make a slurry of crude compound having Formula IV in 20% H₂O/IPA (based on Karl Fischer analysis of the wet solid). The slurry was heated to 69° C. over 1 h. The temperature was maintained at 65° C. for 20 min and the solution was cooled slowly to 50° C. over 50 min. The mixture was then cooled, and the resulting slurry was stirred for 30 min below 10° C. The concentration of the compound having Formula IV was 11.6 mg/mL. The slurry was filtered, and the filter cakes were dried under vacuum at 50° C. for 43 h [589.5 g]: HPLC 93.5% (AUC) and 92.9% (AUC) for separately filtered batches.

The solids were mixed with 2-propanol (3 L) under nitrogen, the slurry was heated to 60° C., and a solution was obtained. The solution was stirred at 60° C. for 15 min and slowly cooled to 52° C. (crystallization occurred at 56.6 0 C). The mixture was further cooled, and the slurry was stirred for 30 min below 10° C. HPLC analysis of the filtrate showed a concentration of 2.8 mg/mL of the compound having Formula IV and the slurry was stirred for an additional 30 min. HPLC analysis of the filtrate showed a concentration of 2.6 mg/mL of the compound having Formula IV. The slurry was filtered, and the filter cake was rinsed with cold 50:50 IPA/water (2×580 mL) over 17 h and the filter cake was dried under vacuum at 50° C. for 20 h to afford pure compound having Formula IV as a brown solid [492.2 g, 53% yield vs limiting reagent compound having Formula III]: HPLC 96.1% (AUC), $t_R$=14.2 min; the $^1$H NMR, $^{19}$F NMR, and $^{13}$C NMR spectra were consistent with the assigned structure ($^1$H NMR (CDCl₃, 300 MHz, ppm): 7.00-7.06 (m, 2H), 6.74-6.80 (m, 2H), 6.63-6.68 (m, 2H), 4.32 (q, J=8.0 Hz, 2H); $^{13}$C NMR (CDCl₃, 75 MHz, ppm): 162.6, 159.3, 156.1, 151.4, 151.3, 127.3, 126.0, 125.9, 123.7, 120.0, 114.1, 111.7, 110.7, 110.4, 104.9, 104.5, 104.1, 65.6, 65.1, 64.6, 64.1; $^{19}$F (CDCl₃, 282 MHz, ppm): −74.3, −114.2). Solvent content determined by the Karl Fischer method was 0.004 wt % H₂O.

Step 3—Synthesis of 3-fluoro-7-(2,2,2-trifluoroethoxy)phenoxathiin-10,10-dioxide Formula IV [491.0 g, 1.55 mol] from above and glacial acetic acid (7.4 L) were combined with stirring under nitrogen. Peracetic acid (35 wt % in acetic acid, 337 g, 1.55 mol) was diluted with glacial acetic acid (337 g). The peracetic acid/acetic acid solution was slowly added to the Formula IV mixture while cooling in an ice bath at a rate such that the temperature remained below 20° C. After 25 min, the reaction mixture was filtered, and the filtrate transferred back into the reaction flask. Peracetic acid (35 wt %, 371 g, 1.70 mol) was added to the reaction mixture over 5 min, keeping the reaction temperature below 20° C. After 10 min, the mixture was heated to 40° C. over 35 min and monitored by HPLC analysis. After 8 h, the mixture was cooled to 34° C. Water (1.7 L) was added to the batch and the mixture continued cooling to 20° C. An aqueous solution of sodium sulfite (196 g of sodium sulfite in 1 L of water) was added over 15 min at a rate such that the reaction temperature remained below 25° C. The resulting yellow slurry was stirred below 25° C. for 30 min. A sample of the filtrate was taken and HPLC analysis showed a concentration of 4.2 mg/mL of 3-fluoro-7-(2,2,2-trifluoroethoxy)phenoxathiin-10,10-dioxide. Water (1 L) was added and the slurry was stirred below 25° C. for 30 min. A sample of the filtrate was taken and HPLC analysis showed a concentration of 3.0 mg/mL of 3-fluoro-7-(2,2,2-trifluoroethoxy)phenoxathiin-10,10-dioxide. Water (1 L) was added and the slurry was stirred below 25° C. for 30 min. A sample of the filtrate was taken and HPLC analysis showed a concentration of 1.6 mg/mL of 3-fluoro-7-(2,2,2-trifluoroethoxy)phenoxathiin-10,10-dioxide. Water (1 L) was added and the slurry was stirred below 25° C. for 30 min. A sample of the filtrate was taken and HPLC analysis showed a concentration of 1.8 mg/mL of 3-fluoro-7-(2,2,2-trifluoroethoxy)phenoxathiin-10,10-dioxide. The slurry was filtered, the filtrate collected, and the solids were rinsed with water (2×2.4 L). The wet solids (1552.8 g) were transferred to two drying trays and dried under vacuum at 50° C. for 10 h to yield 3-fluoro-7-(2,2,2-trifluoroethoxy)phenoxathiin-10,10-dioxide (1070.9 g, solvent content determined by the Karl Fischer method was 55.3 wt % H₂O). The solids were further dried under vacuum at 50° C. for 46.5 h to crude 3-fluoro-7-(2,2,2-trifluoroethoxy)phenoxathiin-10,10-dioxide (506.26 g, 97.7% AUC, Solvent content determined by the Karl Fischer method was 0.15 wt % H₂O). 3-Fluoro-7-(2,2,2-trifluoroethoxy)phenoxathiin-10,10-dioxide [490.3 g] was mixed with acetic acid (2.4 L) under nitrogen. The resulting slurry was heated to reflux (119° C.) over 1 h and stirred for 5 min. The solution was slowly cooled over 5.5 h to 23° C. The resulting slurry was stirred below 23° C. for 30 min. The solids were filtered, rinsed with acetic acid (490 mL, 1 vol) and water (2×490 mL), and dried overnight under vacuum at 50° C. to yield pure 3-fluoro-7-(2,2,2-trifluoroethoxy)phenoxathiin-10,10-dioxide as an off-white solid [394.27 g, 73% yield from the compound of Formula IV]: HPLC 99.4% (AUC), $t_R$=11.6 min. The $^1$H NMR, $^{19}$F NMR, and $^{13}$C NMR spectra were consistent with the assigned structure ($^1$H NMR (CDCl₃, 300 MHz, ppm): 7.98-8.08 (m, 2H), 7.00-7.18 (m, 3H), 6.89 (d, J=2.5 Hz, 1H), 4.45 (q, J=8.0 Hz, 2H); $^{13}$C NMR (CDCl₃, 75 MHz, ppm): 167.4, 164.0, 161.6, 153.4, 153.3, 126.3, 126.1, 125.8, 124.9, 122.2, 122.2, 121.3, 119.7, 114.0, 113.7, 113.5, 106.7, 106.3, 104.3, 67.0, 66.5, 66.0, 65.5; $^{19}$F (CDCl₃, 282 MHz, ppm): −74.0, −101.9). Solvent content determined by the Karl Fischer method was 0.04 wt % H₂O.

Example 3

This example provides a comparison of the 3-fluoro-7-(2,2,2-trifluoroethoxy)phenoxathiin-10,10-dioxide prepared in Example 1 (containing Form A) with the 3-fluoro-7-(2,2,2-trifluoroethoxy)phenoxathiin-10,10-dioxide prepared in Example 2 (containing Form B).

Using a standard differential scanning calorimetry technique, the products of Examples 1 and 2 were examined. The product of Example 1 displayed a smaller peak at 161.8° C. and a larger peak at 171.0° C. The product of Example 2 displayed a single peak at 162.6° C. Based on these observations, the product of Example 1 was considered to contain a high melting temperature form (termed Form A) and smaller amount of a low melting temperature form (termed Form B), while the product of Example 2 was considered to contain only the low melting temperature form, Form B.

Figure 1B:
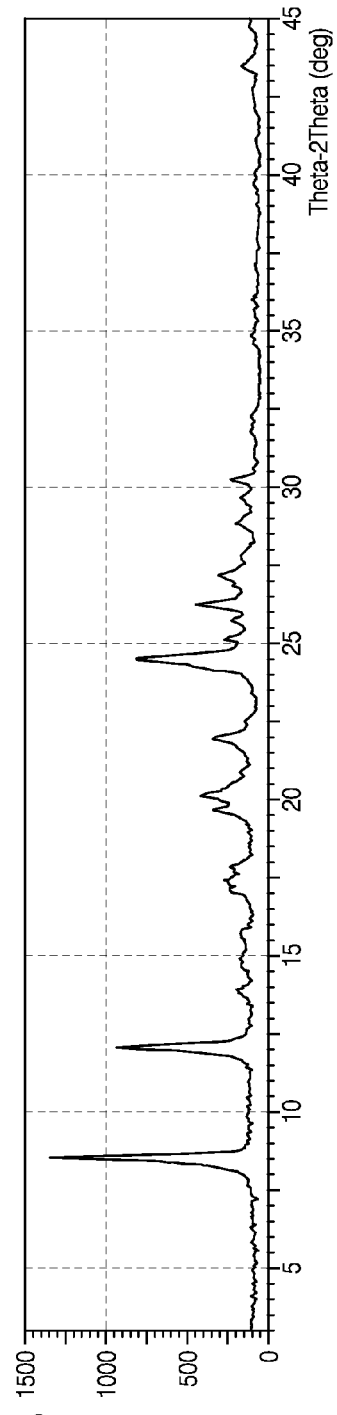
Figure 1C:
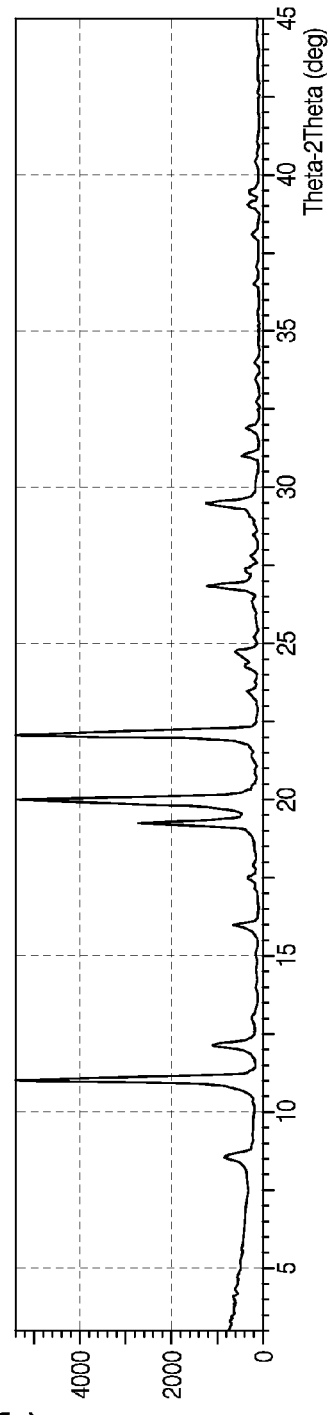

Using a standard powder x-ray diffraction technique, the products of Examples 1 and 2 were examined. The resulting diffraction pattern for the product of Example 1 is seen in FIG. 1(c), and the resulting diffraction pattern for the product of Example 2 (Form B) is seen in FIG. 1(b). FIG. 1(c) contains peaks that also are present in FIG. 1(b), and also contains peaks not present in FIG. 1(b)—such peaks are the peaks of Form A, depicted in FIG. 1(a). For example, peaks at 2θ=8.5° and 12.0° are present as major peaks in FIG. 1(b) and as minor peaks in FIG. 1(a), and the peak at 2θ=11.0° in FIG. 1(c) is absent in FIG. 1(b), but present in FIG. 1(a). Thus, FIG. 1(c) is consistent with the presence of a mixture of forms of 3-fluoro-7-(2,2,2-trifluoroethoxy)phenoxathiin-10,10-dioxide in the product of Example 1, where the minor component is Form B, which is the product of Example 2, and the major component is Form A.

Figures 2A, 2B, 2C:
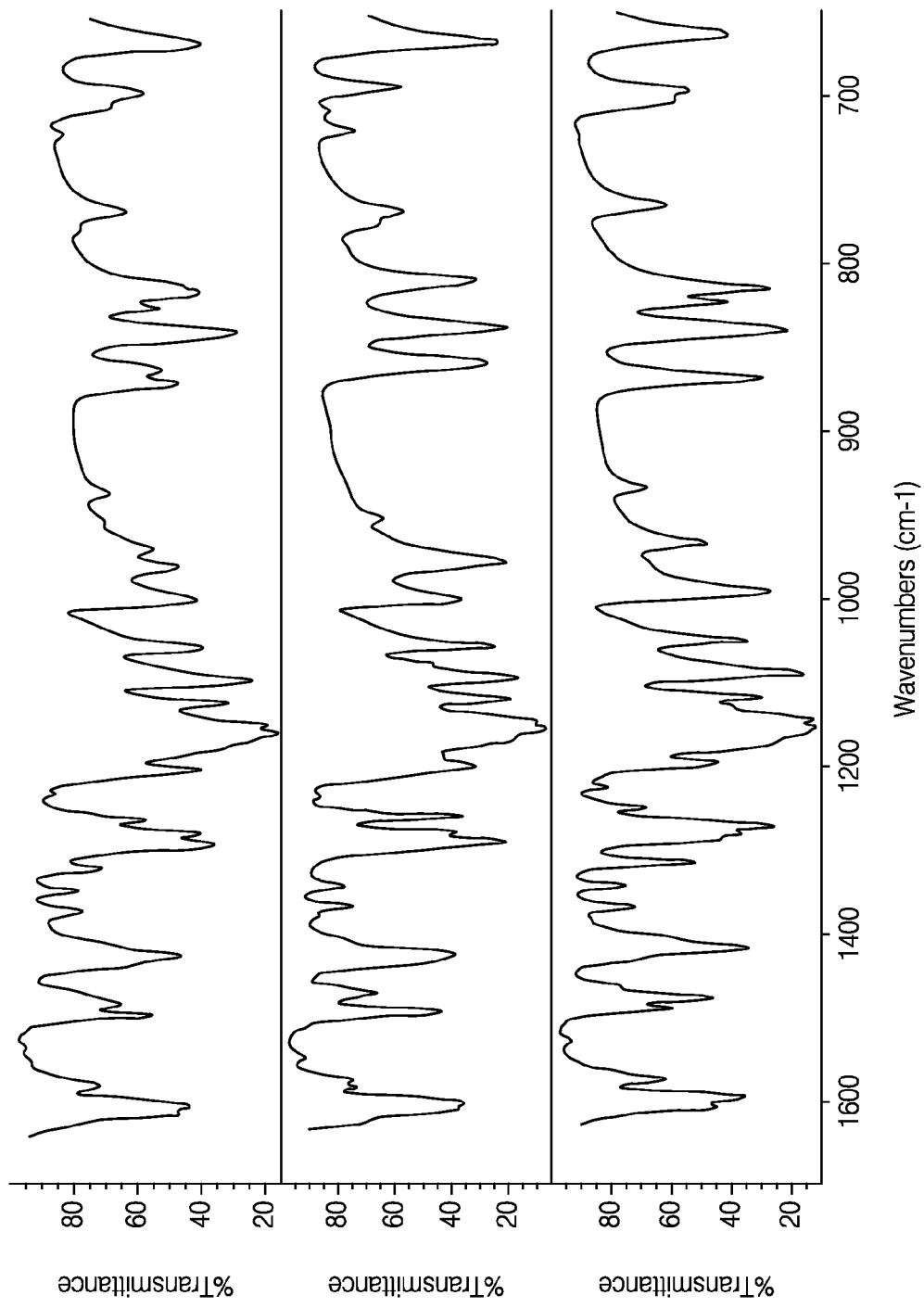
FIG. 2 depicts attenuated total reflectance Fourier transform infrared spectra of Form A (FIG. 2(a)) and Form B (FIG. 2(b)) of 3-fluoro-7-(2,2,2-trifluoroethoxy)phenoxathin 10,10-dioxide, and the product of 3-fluoro-7-(2,2,2-trifluoroethoxy)phenoxathin 10,10-dioxide synthesis as provided in Example 1 (FIG. 2(c)).

Using a standard attenuated total reflectance Fourier transform infrared spectroscopy technique, the products of Examples 1 and 2 were examined. As seen in FIG. 2, differences between the product of Example 1 (FIG. 2(c)) and the product of Example 2 (FIG. 2(b)) are most pronounced in the regions 1480-1440 cm$^{-1}$ and 970-800 cm$^{-1}$. Similarly, differences between Form A (FIG. 2(a)) and Form B (FIG. 2(b)) are most pronounced in the regions 1480-1440 cm$^{-1}$ and 970-800 cm$^{-1}$.

Example 4

This example provides a method for converting the 3-fluoro-7-(2,2,2-trifluoroethoxy)phenoxathiin-10,10-dioxide prepared in Example 2 to a high-melting form of 3-fluoro-7-(2,2,2-trifluoroethoxy)phenoxathiin-10,10-dioxide consistent with Form A.

A crystalline sample of 414 mg of the 3-fluoro-7-(2,2,2-trifluoroethoxy)phenoxathiin-10,10-dioxide prepared in Example 1 was stirred in 4 mL of H$_2$O at room temperature for 15.5 hours. The sample was then filtered, kept at ambient temperature for 1½ days, and vacuum dried at 50° C. for 66 hours. Differential scanning calorimetry of the dried product showed a single melting point at 170.3° C.

Example 5

This example provides a method for preparing Form A 3-fluoro-7-(2,2,2-trifluoroethoxy)phenoxathiin-10,10-dioxide from a solution of 3-fluoro-7-(2,2,2-trifluoroethoxy)phenoxathiin-10,10-dioxide.

In a heating well, 6, 7-mL scintillation vials were prepared with stir bars and charged with approximately 100 mg of the 3-fluoro-7-(2,2,2-trifluoroethoxy)phenoxathiin-10,10-dioxide prepared in accordance with the method presented in Example 4. To vials 1-3 and 4-6, 500 µL of acetic acid with varied percentages of water (0%, 5%, 10%, 0%, 5%, and 10%, respectively) were added. The vials were heated to 100° C., and maintained that that temperature for 5 minutes. Vials 1-3 were ramp-cooled at 20° C./hr and collected by filtration upon reaching 30° C. Vials 4-6 were placed directly into a refrigerator for an hour before being collected by filtration. All filtrations were collected by using a 2 mL water rinse. Recoveries and DSC results are in Table 1. The sample in vial 3 shows only the higher melting solid, Form A.

TABLE 1

| Vial | % water in AcOH | % recov | DSC peaks | Form | Notes |
| --- | --- | --- | --- | --- | --- |
| 1 | 0 | 87.6 | 162, 171 | Mix | Ramp cooled at 20° C./hr |
| 2 | 5 | 85.7 | 164, 172 | Mix | Ramp cooled at 20° C./hr |
| 3 | 10 | 82.3 | 171 | Form A | Ramp cooled at 20° C./hr |
| 4 | 0 | 89.2 | 163, 171 | Mix | Directly into refrigerator |
| 5 | 5 | 87.1 | 163, 171 | Mix | Directly into refrigerator |
| 6 | 10 | 88.8 | 162, 171 | Mix | Directly into refrigerator |

Example 6

This example provides a seeding crystallization method for crystallizing 3-fluoro-7-(2,2,2-trifluoroethoxy)phenoxathiin-10,10-dioxide as Form A.

Approximately 200 mg of the product of Example 1 was charged to each of 5 vials (7-mL scintillated) with magnetic stir bars and in heating wells equipped with a J-Kem, and slurried in 1.8 mL of either 5% or 10% water in acetic acid (see Table 1). All 5 vials were heated to 105° C., at which point they appeared completely clear. After 5 min at 105° C., the contents of each vial were filtered through a Millex FH 0.45 µm syringe filter to a clean, pre-heated vial. All 5 vials were clear at this temperature; vials 1-4 became hazy upon being seeded with 2 weight % of 3-fluoro-7-(2,2,2-trifluoroethoxy)phenoxathiin-10,10-dioxide prepared in accordance with the method presented in Example 4. Reaction 5 was a control experiment with no seeds added. Vials 1 and 2 were cooled after seeding at 20° C. per hour and vials 3, 4, and 5 were held at 75° C. for 30 minutes before being cooled at the same rate. All 5 vials were cooled to room temperature before being vacuum filtered on Whatman Number 1 filter paper and rinsed with about 1 mL of the same solvent used for the recrystallization. Vials 1-4 were all high-melt forms of 3-fluoro-7-(2,2,2-trifluoroethoxy)phenoxathiin-10,10-dioxide, while vial 5, the only unseeded batch, produced only the low-melting crystalline form (see Table 2). The recovery for these 5 experiments ranged from 77-81%.

TABLE 2

| Vial | Amount (mg) | % water in AcOH | Temp ° C. | % recov | DSC peak | Form | Notes |
| --- | --- | --- | --- | --- | --- | --- | --- |
| 1 | 200.7 | 5 | 105 | 80.72 | 171 | Form A | Seeded at 75° C., then cooled at a rate of 20° C./hr |
| 2 | 204.8 | 10 | 105 | 81.05 | 171 | Form A | |
| 3 | 207.3 | 5 | 105 | 80.56 | 171 | Form A | Seeded at 75° C., temp held for 30 min, then cooled at 20° C./hr |
| 4 | 195.7 | 10 | 105 | 79.26 | 171 | Form A | |
| 5 | 209.4 | 5 | 105 | 76.87 | 162 | Form B | No seeds, held at 75° C. for 30 min, then cooled at 20° C./hr |

Example 7

This example describes quantitation of Forms A and B of 3-fluoro-7-(2,2,2-trifluoroethoxy)phenoxathiin-10,10-dioxide using FTIR.

Figure 7:
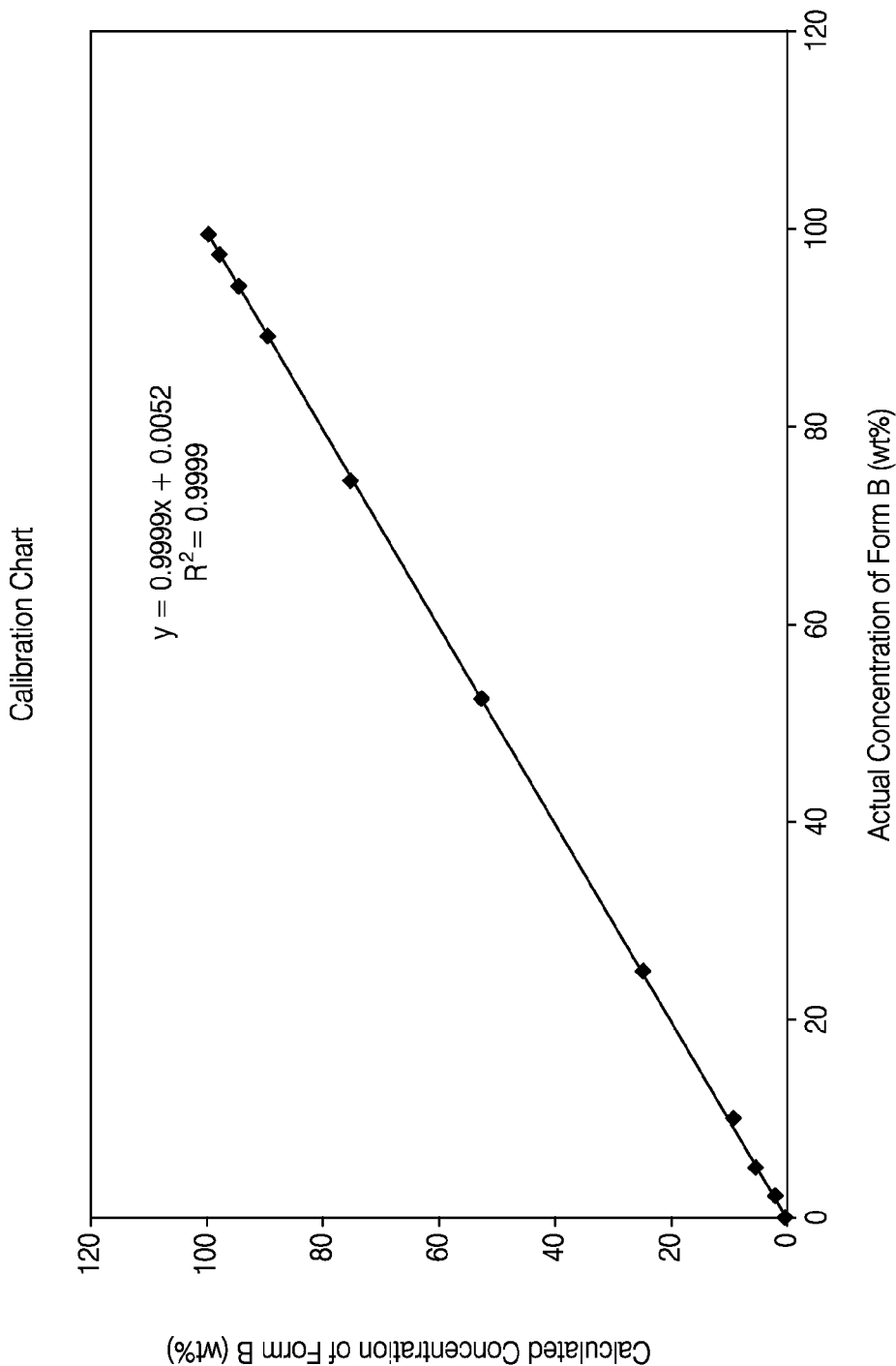
FIG. 7 depicts a calibration curve for quantitating relative amounts of Form A and Form B of 3-fluoro-7-(2,2,2-trifluoroethoxy)phenoxathiin-10,10-dioxide using ATR-FTIR.

As seen in FIG. 2, differences can be observed between Forms A and B of 3-fluoro-7-(2,2,2-trifluoroethoxy)phenoxathiin-10,10-dioxide using ATR-FTIR. FTIR spectra were obtained for standard mixtures of Forms A and B of 3-fluoro-7-(2,2,2-trifluoroethoxy)phenoxathiin-10,10-dioxide as listed in Table 3 using the ATR (attenuated total reflectance) accessory. The stack plot of IR spectra (see, e.g., FIG. 2) showed that Forms A and B have several unique absorbance peaks between 950 and 650 cm$^{-1}$, but the peaks are mostly overlapping. Therefore, a simple Beer's law analysis, which requires distinct peaks for each form, is less suited for quantitative analysis. More complicated algorithms were applied to the data and the Partial Least Squares (PLS) method using TQ Analyst v 7.1 (Thermo Electron Corporation, Waltham, Mass.) was found to provide the best result. A calibration curve was generated using known amounts of pure Form A and pure Form B as summarized in Table 3, where "Theoretical" refers to intended mass of the polymorph to be used for a given point on the calibration curve and "Actual" refers to actual mass. The calibration curve obtained using these standard form mixtures is shown in FIG. 7. The high linearity, a slope of nearly 1.0, and Y intercept near 0 confirms the accuracy of the method throughout the range. The error associated with Form A and Form B concentration determined from the model was observed to be about ±1%. Table 4 shows the difference for each data point used between the actual weight percentage of Form B used in each sample compared to the amount calculated using the calibration curve.

TABLE 3

| Theoretical | | Form B Mass | | Form A Mass | | Actual Ratio | |
|---|---|---|---|---|---|---|---|
| Low (wt %) | High (wt %) | Theo. (mg) | Actual (mg) | Theo. (mg) | Actual (mg) | Low (wt %) | High (wt %) |
| 0 | 100 | 0.0 | 0.0 | 40 | 40.5 | 0.00 | 100.00 |
| 2 | 98 | 1.0 | 1.082 | 49.0 | 49.043 | 2.16 | 97.84 |
| 5 | 95 | 2.5 | 2.537 | 47.5 | 47.751 | 5.04 | 94.96 |
| 10 | 90 | 5.0 | 5.048 | 45.0 | 45.008 | 10.08 | 89.92 |
| 25 | 75 | 12.5 | 12.497 | 37.5 | 37.536 | 24.98 | 75.02 |
| 50 | 50 | 25.0 | 27.823 | 25.0 | 24.863 | 52.81 | 47.19 |
| 75 | 25 | 37.5 | 37.828 | 12.5 | 12.544 | 75.10 | 24.90 |
| 90 | 10 | 45.0 | 45.042 | 5.0 | 5.156 | 89.73 | 10.27 |
| 95 | 5 | 47.5 | 47.579 | 2.5 | 2.592 | 94.83 | 5.17 |
| 98 | 2 | 49.0 | 48.983 | 1.0 | 0.998 | 98.00 | 2.00 |
| 100 | 0 | 40.0 | 40.1 | 0.0 | 0.0 | 100.00 | 0.00 |

TABLE 4

| Actual Form B (wt %) | Calculated Form B (wt %) | Difference (wt %) |
|---|---|---|
| 0.00 | 0.39 | 0.39 |
| 2.16 | 2.03 | −0.13 |
| 5.04 | 5.45 | 0.41 |
| 10.08 | 9.30 | −0.78 |
| 24.98 | 24.99 | 0.01 |
| 52.81 | 52.75 | −0.06 |
| 75.10 | 75.53 | 0.43 |
| 89.73 | 89.63 | −0.10 |
| 94.83 | 94.74 | −0.09 |
| 98.00 | 98.00 | 0.00 |
| 100.00 | 99.94 | −0.06 |

Example 8

This example describes refinement of dispersion pressure and reproducibility in forming particles of Form A of 3-fluoro-7-(2,2,2-trifluoroethoxy)phenoxathiin-10,10-dioxide that are not fractured and have RSD values within acceptable range specified by U.S. Pharmacopeia <429> "Light Diffraction Measurement of Particle Size."

Dispersion was performed on a sample of Form A of 3-fluoro-7-(2,2,2-trifluoroethoxy)phenoxathiin-10,10-dioxide produced accordance with the method presented in Example 4. Dispersion pressure of 0.5 to 2.0 bar was used to disperse the sample particles. Samples were analyzed by microscopy prior to particle size analysis to assess aggregation and estimate particle size, and without fracturing primary particles or causing aggregation. Dispersion pressure of 0.5 to 1.0 bar was shown to be optimum pressure for Form A, giving acceptable particle sizes. Particle size was measured using a Sympatec HELOS equipped with VIERI dry powder feeder unit, and sample measurements for optimization of jet pressure and repeatability were performed according to USP<429>, Method Validation Protocol ANC00756, and TM-1509 Rev.00 (draft). Measured particle sizes are provided in Table 5.

TABLE 5

| Dispersion Pressure (bar) | $x_{10}$ (μm) | $x_{50}$ (μm) | $x_{90}$ (μm) |
|---|---|---|---|
| 0.5 | 3.05 | 9.07 | 24.49 |
| 1 | 2.54 | 7.96 | 19.32 |
| 1.5 | 2.21 | 7.35 | 17.1 |
| 2 | 1.94 | 6.88 | 15.32 |

Since modifications will be apparent to those of skill in this art, it is intended that this invention be limited only by the scope of the appended claims.

What is claimed is:

1. A polymorphic form of 3-fluoro-7-(2,2,2-trifluoroethoxy)phenoxathiin-10,10-dioxide, characterized as having a melting point at about 169-175° C.

2. A polymorphic form of 3-fluoro-7-(2,2,2-trifluoroethoxy)phenoxathiin-10,10-dioxide, characterized as being in crystalline form and having an x-ray powder diffraction peak at 2θ=11.0°, using $CuK_\alpha$ radiation.

3. The polymorphic form of claim 2, further characterized as having x-ray powder diffraction peaks at 2θ=20.1° and/or 22.2°, using $CuK_\alpha$ radiation.

4. The polymorphic form of 3-fluoro-7-(2,2,2-trifluoroethoxy)phenoxathiin-10,10-dioxide of claim 2, further characterized as having an x-ray powder diffraction pattern substantially identical to FIG. 1(a).

5. A polymorphic form of 3-fluoro-7-(2,2,2-trifluoroethoxy)phenoxathiin-10,10-dioxide, characterized as having an attenuated total reflectance Fourier transform infrared spectrum at 1480-1440 $cm^{-1}$ substantially identical to FIG. 2(a).

6. The polymorphic form of 3-fluoro-7-(2,2,2-trifluoroethoxy)phenoxathiin-10,10-dioxide of claim 5, characterized as having an attenuated total reflectance Fourier transform infrared spectrum at 970-800 $cm^{-1}$ substantially identical to FIG. 2(a).

7. The polymorphic form of 3-fluoro-7-(2,2,2-trifluoroethoxy)phenoxathiin-10,10-dioxide of claim 1, characterized as dissolving at about 75-85° C. in a solution of 10% (v/v) water in acetic acid.

8. A composition, wherein at least about 0.1%, 0.5%, 1%, 2%, 3%, 4%, 5%, 7%, or 10%, of the total 3-fluoro-7-(2,2,2-trifluoroethoxy)phenoxathiin-10,10-dioxide is in the polymorphic form provided in claim 1.

9. The composition of claim 8, wherein at least about 15%, 20%, 30%, 50%, or 70%, of the total 3-fluoro-7-(2,2,2-trifluoroethoxy)phenoxathiin-10,10-dioxide is in said polymorphic form.

10. The composition of claim 8, wherein at least about 90%, 95%, or 99%, of the total 3-fluoro-7-(2,2,2-trifluoroethoxy)phenoxathiin-10,10-dioxide is in said polymorphic form.

11. A formulation comprising the polymorphic form of claim 1, and a pharmaceutically acceptable carrier.

12. The formulation of claim 11, which is formulated for oral administration.

13. The formulation of claim 11, which is in solid form.

14. The formulation of claim 11, which is a tablet or a capsule.

15. A method for treating a mammal having a medical, psychiatric and/or neurological condition or disorder comprising: (a) identifying a subject in need of treatment for a mammal having a medical, psychiatric and/or neurological condition; and (b) administering to the subject a pharmaceutically effective amount of the polymorphic form of claim 1.

16. A compound comprising 3-fluoro-7-(2,2,2-trifluoroethoxy)phenoxathiin or a solvate or a hydrate thereof.

17. The 3-fluoro-7-(2,2,2-trifluoroethoxy)phenoxathiin of claim 16 in substantially pure form.

* * * * *